US008827990B2

(12) United States Patent
Van Valen et al.

(10) Patent No.: US 8,827,990 B2
(45) Date of Patent: Sep. 9, 2014

(54) METHODS FOR TREATING EYE CONDITIONS

(71) Applicant: BIOLASE, Inc., Irvine, CA (US)

(72) Inventors: Marcia Van Valen, Aliso Viejo, CA (US); William E. Brown, Jr., Roswell, GA (US)

(73) Assignee: BIOLASE, Inc., Irvine, CA (US)

( * ) Notice: Subject to any disclaimer, the term of this patent is extended or adjusted under 35 U.S.C. 154(b) by 0 days.

(21) Appl. No.: 13/630,971

(22) Filed: Sep. 28, 2012

(65) Prior Publication Data

US 2013/0085484 A1 Apr. 4, 2013

Related U.S. Application Data

(60) Provisional application No. 61/541,017, filed on Sep. 29, 2011.

(51) Int. Cl.
*A61B 18/18* (2006.01)
*A61B 18/20* (2006.01)
*A61F 9/008* (2006.01)
*A61N 5/06* (2006.01)
*A61B 19/00* (2006.01)

(52) U.S. Cl.
CPC ............ *A61B 18/20* (2013.01); *A61B 18/18* (2013.01); *A61F 9/00825* (2013.01); *A61N 5/062* (2013.01); *A61F 2009/00868* (2013.01); *A61B 19/5202* (2013.01); *A61N 2005/0651* (2013.01); *A61N 5/0619* (2013.01); *A61F 2009/00891* (2013.01); *A61F 9/00802* (2013.01)
USPC ........................................ 606/6; 606/4; 606/5

(58) Field of Classification Search
USPC ........................................................ 606/4–6
See application file for complete search history.

(56) References Cited

U.S. PATENT DOCUMENTS

| | | | |
|---|---|---|---|
| 5,222,952 A * | 6/1993 | Loertscher | 606/6 |
| 5,439,462 A | 8/1995 | Bille et al. | |
| 5,549,598 A * | 8/1996 | O'Donnell, Jr. | 606/6 |
| 5,643,250 A | 7/1997 | O'Donnell | |
| 5,919,186 A | 7/1999 | Bath | |
| 6,142,990 A * | 11/2000 | Burk | 606/6 |
| 6,389,193 B1 | 5/2002 | Kimmel et al. | |
| 6,567,582 B1 | 5/2003 | Rizoiu et al. | |
| 6,623,477 B1 | 9/2003 | Elbrecht et al. | |
| 6,743,221 B1 | 6/2004 | Hobart et al. | |
| 7,384,419 B2 | 6/2008 | Jones et al. | |
| 7,421,186 B2 | 9/2008 | Boutoussov et al. | |
| 7,620,290 B2 | 11/2009 | Rizoiu et al. | |

(Continued)

OTHER PUBLICATIONS

Non-Final Office Action dated Jun. 18, 2013 issued in related/corresponding U.S. Appl. No. 13/630,971, filed Sep. 28, 2012.

(Continued)

*Primary Examiner* — William Thomson
*Assistant Examiner* — Sebastian X Lukjan
(74) *Attorney, Agent, or Firm* — Jones Day

(57) ABSTRACT

Systems and methods are provided for reducing intraocular pressure in an eye. A perpendicular incision is made through a conjunctiva of the eye to access a trabecular meshwork of the eye. Electromagnetic energy is focused through the perpendicular incision to ablate a portion of the trabecular network, where said ablation creates a channel for outflow flow of fluid through a sclera venous sinus to reduce pressure within the eye.

22 Claims, 13 Drawing Sheets

(56) References Cited

U.S. PATENT DOCUMENTS

| | | |
|---|---|---|
| 7,665,467 B2 | 2/2010 | Jones et al. |
| 7,751,895 B2 | 7/2010 | Jones et al. |
| 7,785,321 B2 * | 8/2010 | Baerveldt et al. ............... 606/6 |
| 7,878,204 B2 | 2/2011 | Van Valen et al. |
| 8,241,035 B2 | 8/2012 | Jones et al. |
| 2003/0093149 A1 | 5/2003 | Glazier |
| 2006/0195076 A1 * | 8/2006 | Blumenkranz et al. ............ 606/4 |
| 2006/0216329 A1 | 9/2006 | Peyman |
| 2006/0271025 A1 * | 11/2006 | Jones et al. ...................... 606/4 |
| 2007/0042315 A1 | 2/2007 | Boutoussov et al. |
| 2007/0043340 A1 | 2/2007 | Thyzel |
| 2008/0033407 A1 | 2/2008 | Jones et al. |
| 2008/0097416 A1 | 4/2008 | Jones et al. |
| 2008/0161781 A1 | 7/2008 | McArdle et al. |
| 2008/0269731 A1 | 10/2008 | Swinger et al. |
| 2008/0319427 A1 | 12/2008 | Palanker |
| 2009/0062779 A1 | 3/2009 | Rizoiu et al. |
| 2009/0298004 A1 | 12/2009 | Rizoiu et al. |
| 2010/0042082 A1 | 2/2010 | Rizoiu et al. |
| 2011/0059417 A9 | 3/2011 | Rizoiu et al. |
| 2011/0077626 A1 | 3/2011 | Baerveldt et al. |
| 2011/0172650 A1 | 7/2011 | Jones et al. |
| 2012/0135368 A1 | 5/2012 | Rizoiu et al. |

OTHER PUBLICATIONS

International Search Report and Written Opinion dated Feb. 5, 2013 from related/corresponding PCT Patent Application Serial No. PCT/US12/58009, filed Sep. 28, 2012.

Non-Final Office Action dated May 7, 2013 issued in related/corresponding U.S. Appl. No. 13/633,505, filed Oct. 2, 2012.

International Search Report and Written Opinion dated Dec. 24, 2012 from related/corresponding PCT Patent Application Serial No. PCT/US12/58455, filed Oct. 2, 2012.

Final Office Action dated Dec. 18, 2013 from related/corresponding U.S. Appl. No. 13/633,505, filed Oct. 2, 2012.

International Search Report and Written Opinion dated Dec. 24, 2012 from related/corresponding PCT Patent Appl. Serial No. PCT/US12/58455, filed Oct. 2, 2012.

* cited by examiner

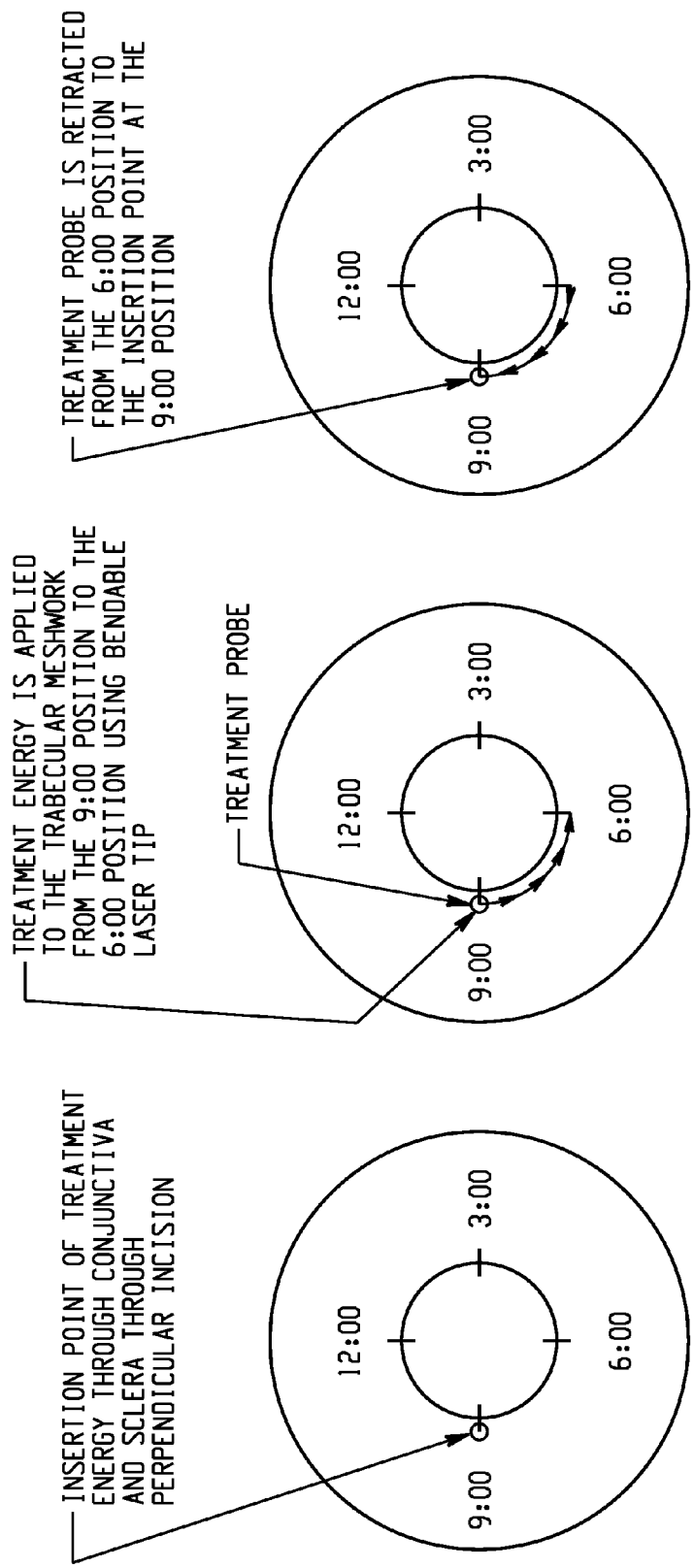

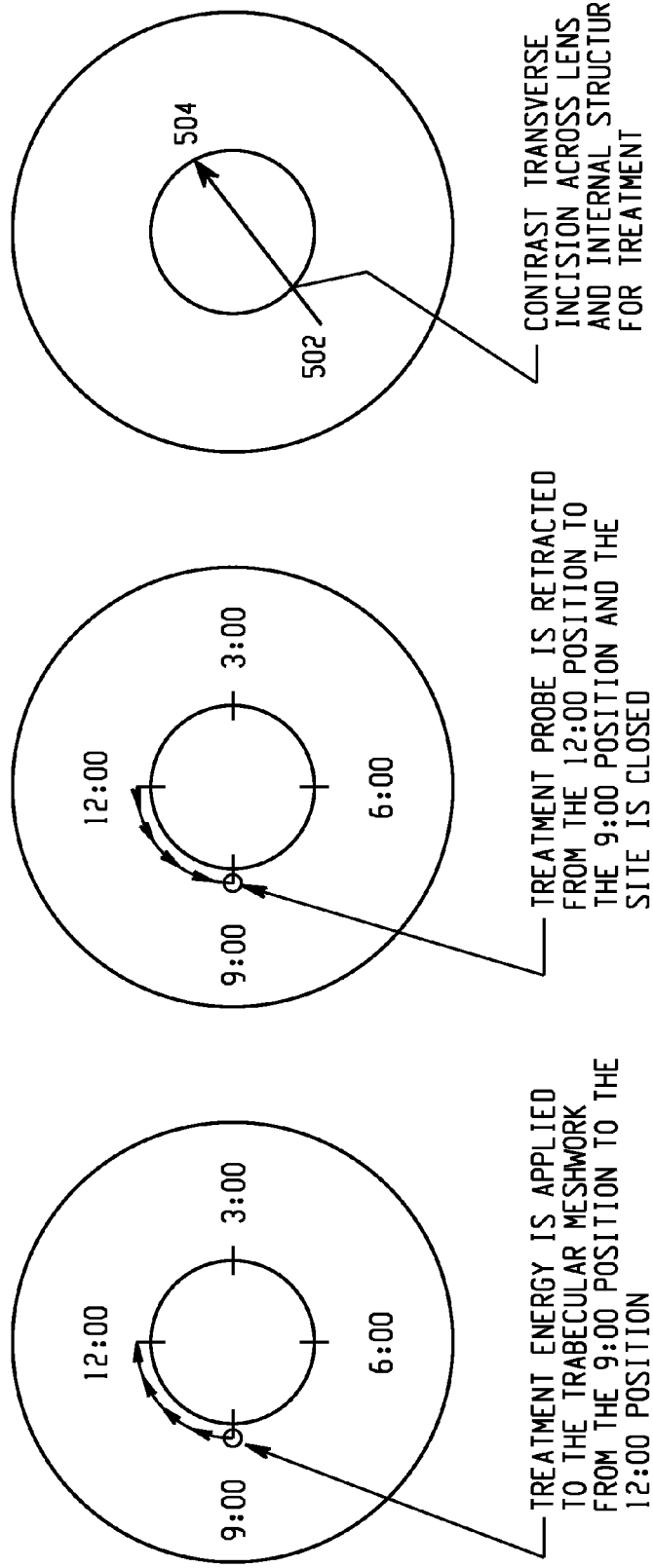

TREATMENT GROUPING

TREATMENT GROUPING

TREATMENT GROUPING

TREATMENT GROUPING

METHODS FOR TREATING EYE CONDITIONS

CROSS-REFERENCE TO RELATED APPLICATIONS

This application claims priority to U.S. Provisional Patent Application No. 61/541,017 filed Sep. 29, 2011, and entitled "Methods for Treating Eye Conditions," the entirety of which is herein incorporated by reference.

BACKGROUND OF THE INVENTION

1. Field of the Invention

The present invention relates generally to medical treatments and, more particularly, to methods and apparatus for treating eye disorders such as glaucoma using energies including laser energies.

2. Description of Related Art

Glaucoma is an eye disorder in which the optic nerve suffers damage, permanently damaging vision in the affected eye(s) and progressing to complete blindness if untreated. It is often, but not always, associated with increased pressure of the fluid in the eye (aqueous humor). The term 'ocular hypertension' is used for cases having constantly raised intraocular pressure (IOP) without any associated optic nerve damage. Conversely, the term 'normal' or 'low tension glaucoma' is suggested for the typical visual field defects when associated with a normal or low IOP.

The nerve damage involves loss of retinal ganglion cells in a characteristic pattern. There are many different subtypes of glaucoma, but they can all be considered a type of optic neuropathy. Raised intraocular pressure is a significant risk factor for developing glaucoma (above 21 mmHg). One person may develop nerve damage at a relatively low pressure, while another person may have high eye pressure for years and yet never develop damage. Untreated glaucoma leads to permanent damage of the optic nerve and resultant visual field loss, which can progress to blindness.

Glaucoma can be divided roughly into two main categories, "open angle" and "closed angle" glaucoma. Closed angle glaucoma can appear suddenly and is often painful; visual loss can progress quickly, but the discomfort often leads patients to seek medical attention before permanent damage occurs. Open angle, chronic glaucoma tends to progress at a slower rate at which patients may not even notice they have lost vision until the disease has progressed significantly.

Glaucoma has been nicknamed the "silent thief of sight" because the loss of vision normally occurs gradually over a long period of time, and is often only recognized when the disease is quite advanced. Once lost, this damaged visual field cannot be recovered. Worldwide, it is the second leading cause of blindness. It is also the leading cause of blindness among African Americans. Glaucoma affects one in 200 people aged fifty and younger, and one in 10 over the age of eighty. If the condition is detected early enough, it is possible to arrest the development or slow the progression with medical and surgical means.

SUMMARY OF THE INVENTION

Systems and methods are provided for reducing intraocular pressure in an eye. In one example, a perpendicular incision is made through a conjunctiva of the eye to access a trabecular meshwork of the eye. Electromagnetic energy is focused through the perpendicular incision to ablate a portion of the trabecular network, where said ablation creates a channel for outflow flow of fluid through a sclera venous sinus to reduce pressure within the eye.

In another example, a system for reducing intraocular pressure in an eye includes a visible light pattern generator, the visible light pattern generator being configured to project a visible light pattern onto a portion of the eye. The system further includes a laser tool, where the laser tool being configured to make a perpendicular incision through the conjunctiva of the eye based on the visible light pattern and to focus energy through the perpendicular incision to ablate a portion of a trabecular network of the eye, where said ablation creates a channel for outflow flow of fluid through a sclera venous sinus to reduce pressure within the eye.

BRIEF DESCRIPTION OF THE FIGURES

FIG. 5 depicts the maneuvering of a laser tip through up to and beyond 180 degrees around the lens of an eye without manipulation transverse to the lens.

DETAILED DESCRIPTION OF THE INVENTION

Regarding treatment of glaucoma disease via laser tissue treatments for example, the trabecular meshwork may be treated (e.g., lased) with tissue treatments (e.g., micro-apertures), taking care to attenuate or avoid a distortion of optical characteristics of the tissue surrounding the trabecular meshwork in the process. In an exemplary implementation, sizes, arrangements, depths, and/or other characteristics of tissue treatments (e.g., micro-apertures) can be adjusted so as, for example, to increase aqueous humor flow (e.g., circulation) obstructed by the trabecular meshwork. Following treatment, the eye may be better able to have the correct fluids including the release of aqueous humor into the drainage canal.

Figure 1:
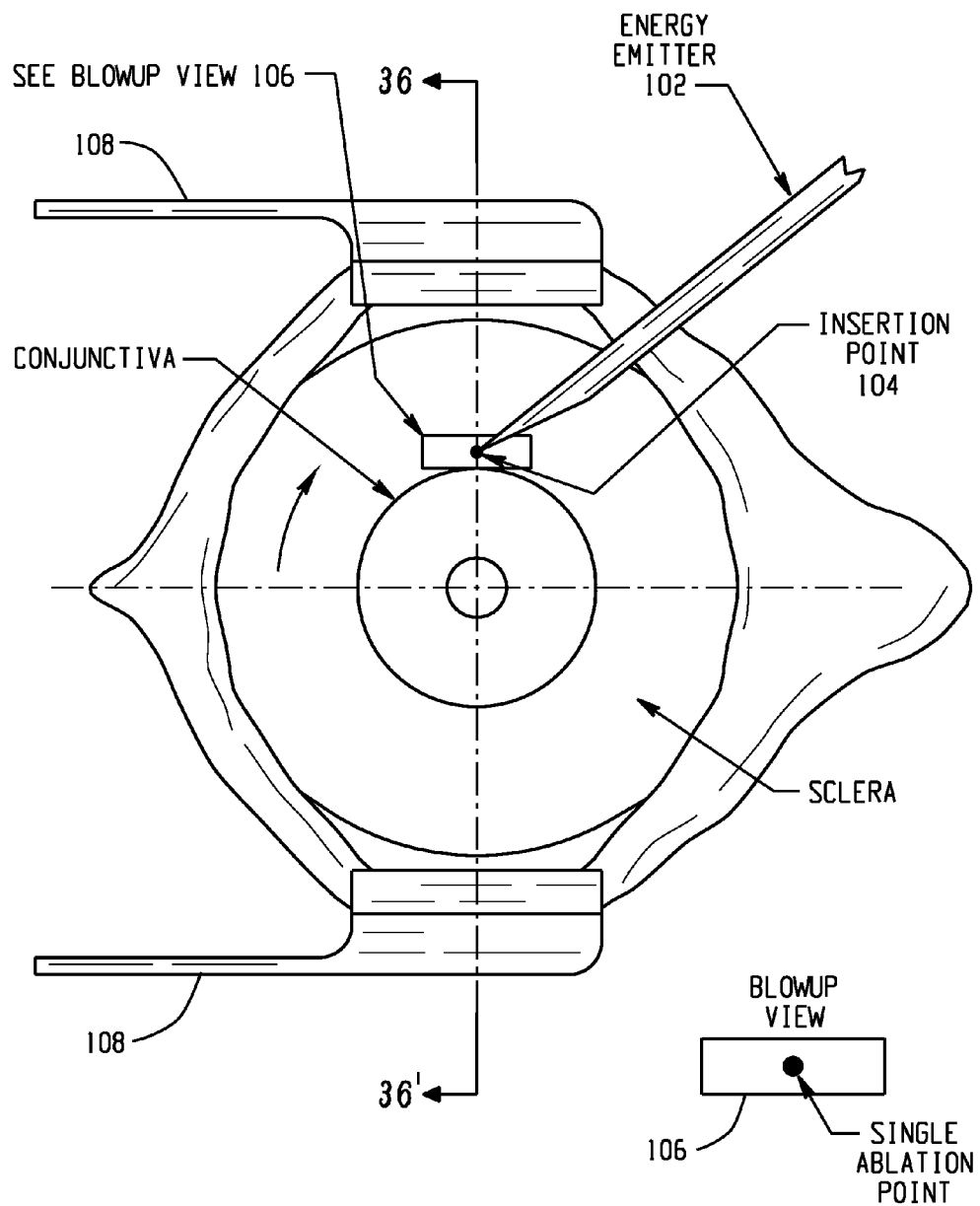
FIG. 1 shows a schematic plan view of the right eye of a patient.
Figure 2:
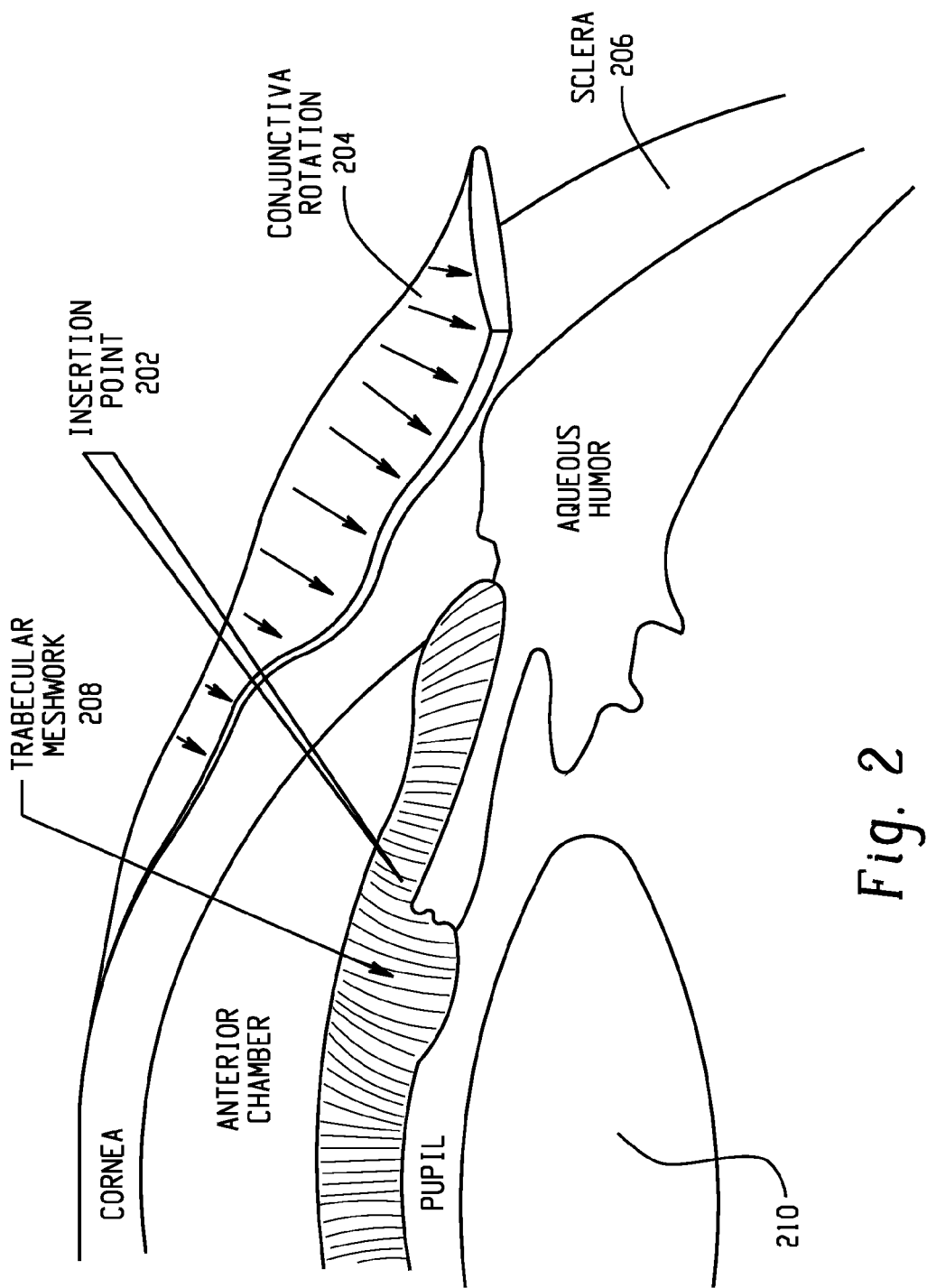
FIG. 2 is a side-elevation view of the eye depicted in FIG. 1.

FIG. 1 shows a schematic plan view of the right eye of a patient, and FIG. 2 is a side-elevation view of the eye depicted in FIG. 1. Tissue treatments (e.g., groupings of tissue treatments) may be applied to portions of, for example, the trabecular meshwork and/or within the tissue surrounding the trabecular meshwork. With reference to FIG. 1, an energy emitter 102, such as an infrared or other laser, is configured to focus energy to ablate certain portions of eye tissue. Such targeted ablations affect a flow of fluid out of the eye through the sclera venous sinus to reduce intraocular pressure of the eye. The energy emitter 102 or other cutting device makes a perpendicular incision through certain top layers of the eye, such as the conjunctiva and the sclera. This incision creates an insertion point 104 for further operations. The energy emitter 102 is configured to focus electromagnetic energy through the perpendicular incision to ablate a portion of the trabecular network. A top view of such an ablation is shown in the blowup view at 106. The depiction of FIG. 1 further includes eyelid braces at 108.

FIG. 2 depicts a cross-sectional view of the eye depicted in FIG. 1 along the 36-36' diameter. The energy emitter or other cutting device creates the insertion point 202 through the conjunctiva 204 and the sclera 206 by making an incision substantially perpendicular to the surface of the eye to provide access to underlying eye structure such as the trabecular meshwork. A portion of the energy emitter, such as a laser tip, is inserted through the insertion point and is used to focus energy on portions of the underlying structure, such as the trabecular meshwork 208, to ablate the focused upon underlying structure. In one example, a portion of the trabecular meshwork is ablated to affect the flow of aqueous humor from the inside of the eye out through the sclera venous sinus, also known as Schlemm's canal. Such aqueous humor may be blocked from flowing by an intact trabecular meshwork 208 resulting in higher than normal intraocular pressure.

The amount and pattern of trabecular meshwork tissue that is ablated can be controlled in part based upon a type of laser tip used for the ablation procedure. Different types of laser tips will focus the electromagnetic energy differently, resulting in different ablation results. For example, an end firing tip may be useful in making focused ablations of the trabecular meshwork, while a side firing or radial tip may be used to make ablations of differing size and shape, such as wider ablations.

Multiple points or whole portions of the trabecular meshwork 208 may be ablated through movement of the laser tip after passage through the perpendicular incision. In one example, the fiber tip includes a flexible fiber end that can be moved in straight or curved directions once inserted through the perpendicular incision. The use of such a flexible fiber enables access to and ablation of significant portions of the trabecular meshwork 208 without any need to traverse the lens 210 of the eye. By avoiding crossing of the lens 210, a procedure is able to avoid collateral damage to the lens, pupil, and other sensitive internal structure of the eye.

In some instances, the conjunctiva may be rotated, such as using a finger or a clamp, prior to making the perpendicular incision through the conjunctiva 204. The conjunctiva 204 is often able to be moved or rotated relative to the sclera 206. When released, the conjunctiva 204 will return to its rested position. By making the perpendicular incision through a rotated portion of the conjunctiva 204, an overlapping of the incision point in the conjunctiva 204 and sclera 206, post treatment, can be avoided. Staggering the healing incision points in this manner promotes healing by providing a healthy conjunctiva 204 covering of the incision point in the sclera 206 and by improving blood flow to the incision point in both the conjunctiva 204 and the sclera 206.

Figure 3:
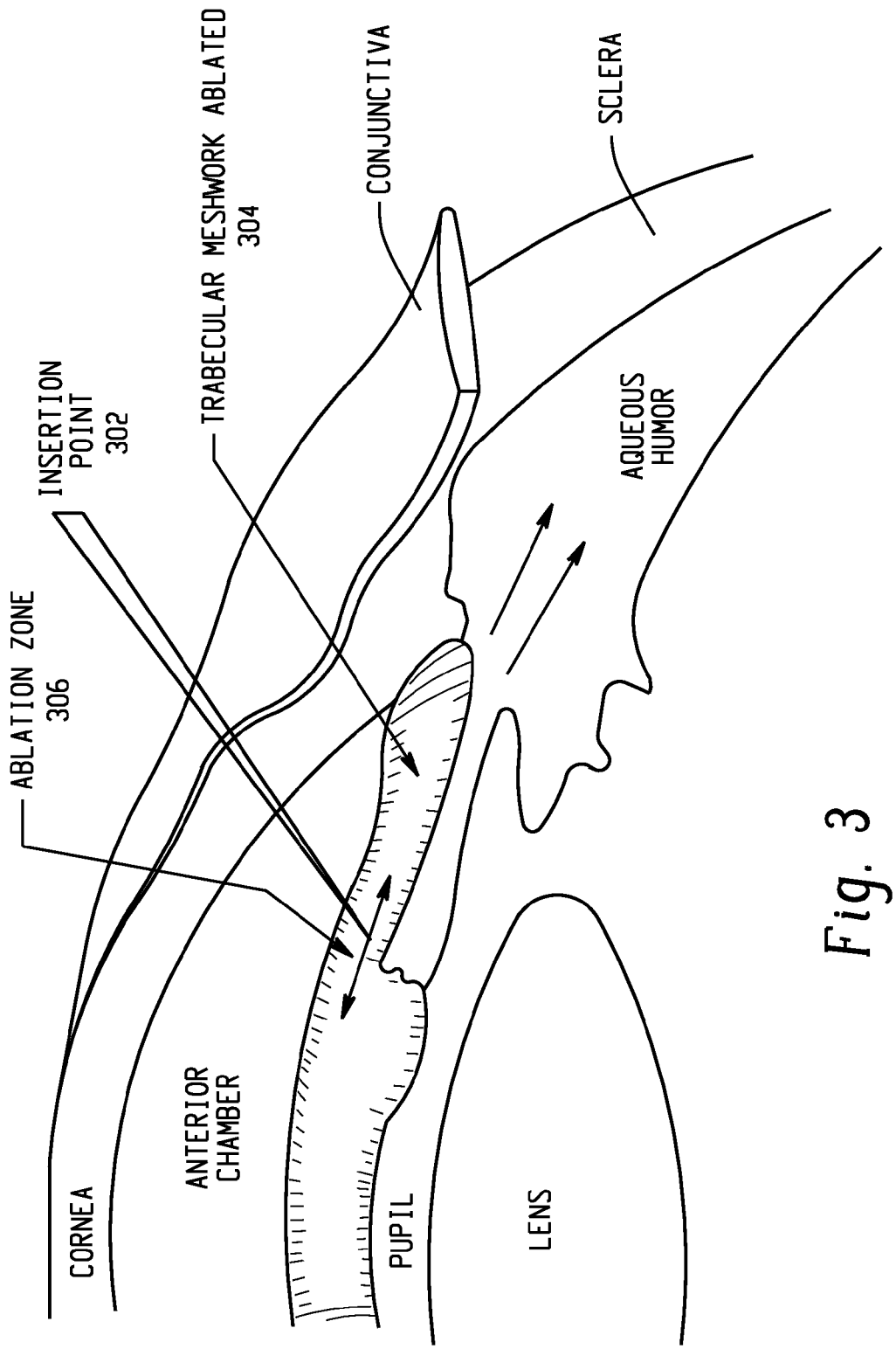
FIG. 3 depicts a cross-sectional view of the eye following ablation of a portion of the trabecular meshwork.
Figure 4:
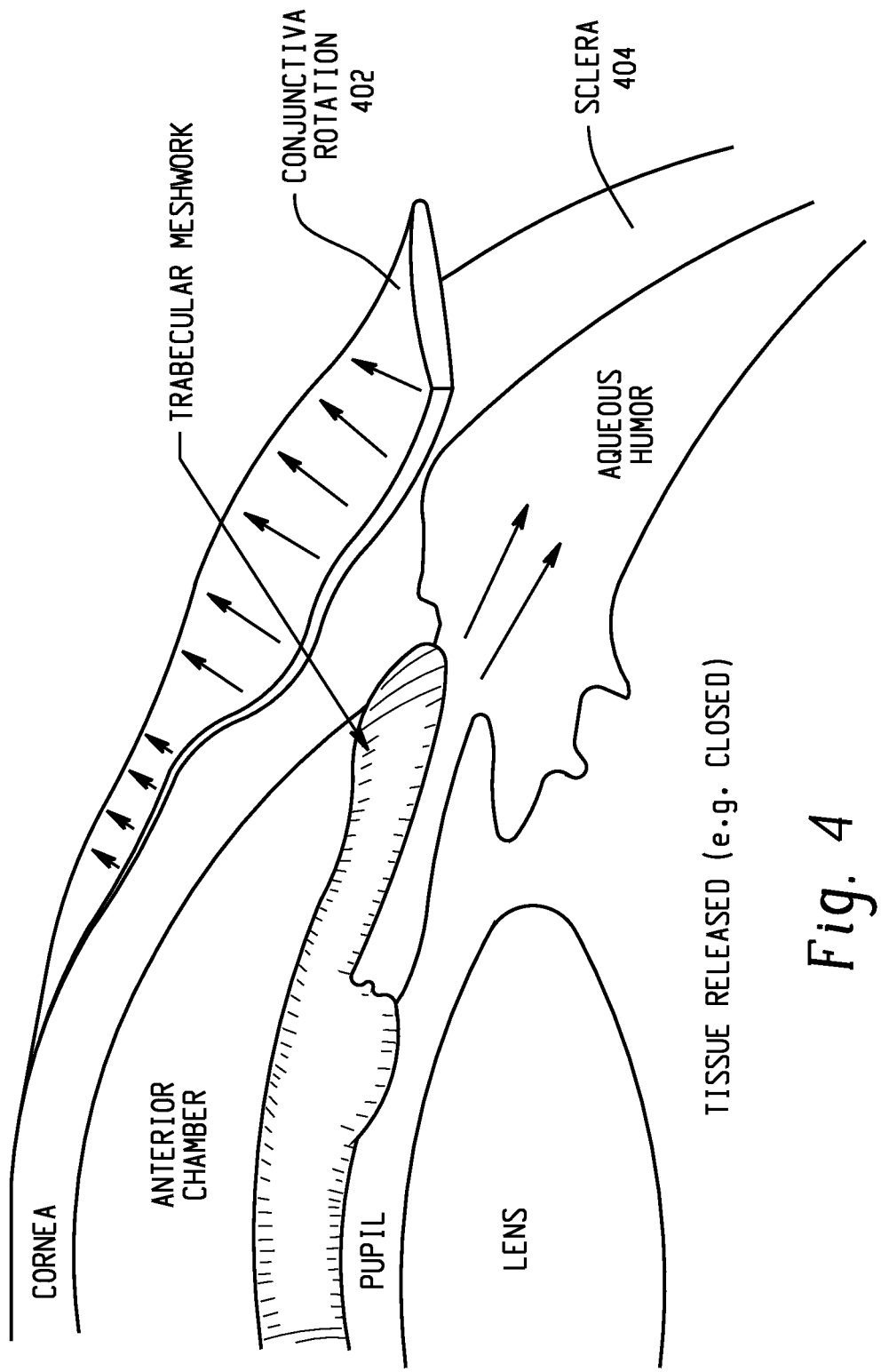
FIG. 4 depicts a cross-sectional view of the eye following release of the conjunctiva from its rotated position, resulting in a staggering of the perpendicular incision through the conjunctiva from the incision through the sclera.

FIG. 3 depicts a cross-sectional view of the eye following ablation of a portion of the trabecular meshwork. After focusing electromagnetic energy through the insertion point 302, a portion of the trabecular meshwork 304 is ablated, resulting in an ablation zone kerf or channel 306. The ablation of the portion of the trabecular meshwork 304 in the ablation zone 306 enables aqueous humor 308 to flow from inside of the eye, resulting in a reduced intraocular pressure and risk of certain degenerative conditions, such as glaucoma. FIG. 4 depicts a cross-sectional view of the eye following release of the conjunctiva 402 from its rotated position, resulting in a staggering of the perpendicular incision through the conjunctiva 402 from the incision through the sclera 404.

FIG. 5 depicts the maneuvering of a laser tip through up to and beyond 180 degrees around the lens of an eye without manipulation transverse to the lens. In FIG. 5a, a perpendicular incision is made through the conjunctiva and sclera at a 9:00 position of the lens of the eye. In FIG. 5b, treatment energy is applied to the trabecular meshwork from the 9:00 position to the 6:00 position using a bendable laser tip. In FIG. 5c, the treatment probe is retracted to the 9:00 position. In FIG. 5d, treatment energy is applied to the trabecular meshwork from the 9:00 position to the 12:00 position. In FIG. 5e, the treatment probe's flexible tip is retracted from the 12:00 position to the 9:00 position, and the treatment site is closed. FIG. 5f is provided to contrast the operations of FIGS. 5a-5e by depicting a transverse incision operation that utilizes a transverse incision at 502 to perform treatment on structure on the far side of the lens at 504. Such an incision and treatment may be necessary when a flexible tip treatment probe is not available. The incision and treatment of FIG. 5f may be considered suboptimal and unsafe because the treatment probe operating transverse across the lens may endanger the lens, pupil, and other internal structure of the eye.

Figure 6A:
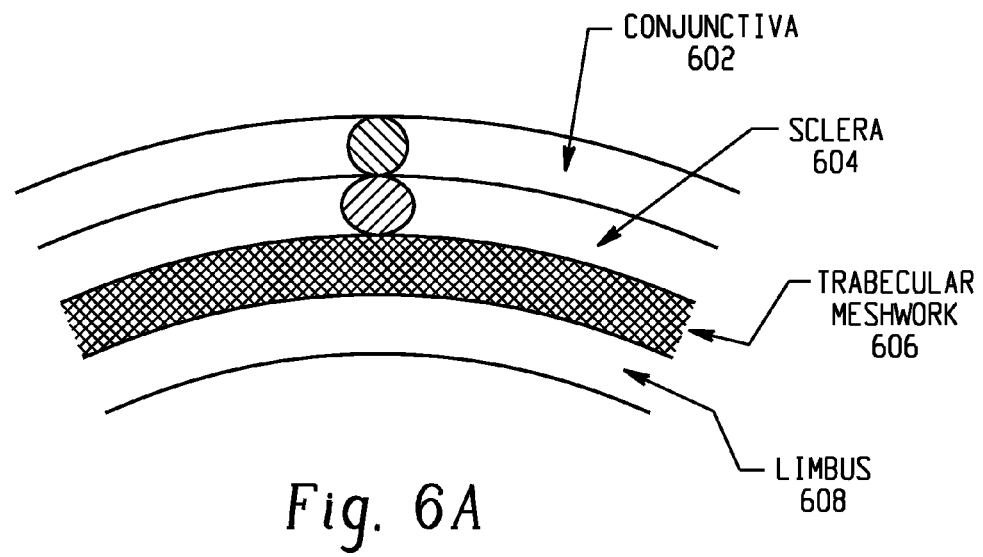
FIGS. 6A and 6B depict the offsetting of incisions in the conjunctiva and the sclera enabled by rotation of the conjunctiva prior to incising.
Figure 6B:
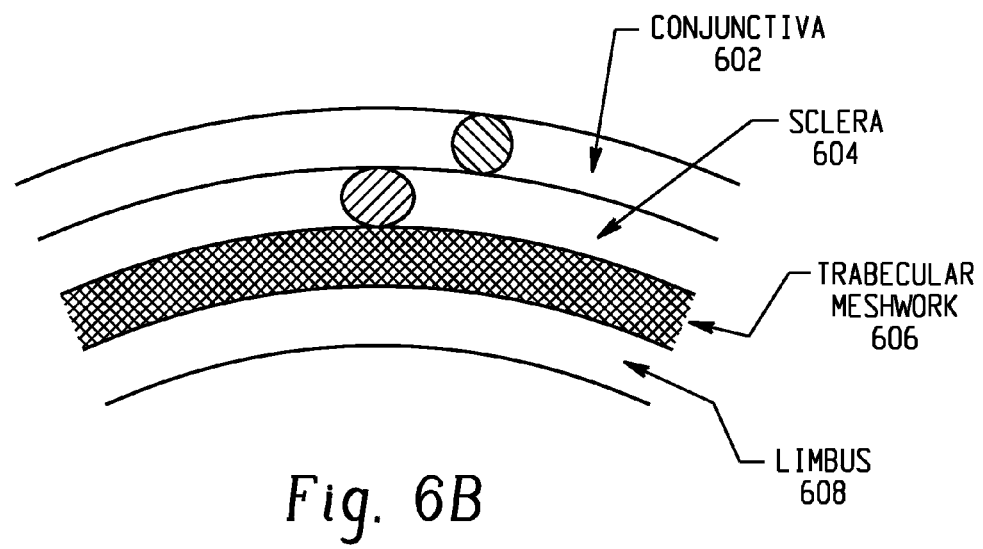

FIGS. 6A and 6B depict the offsetting of incisions in the conjunctiva and the sclera enabled by rotation of the conjunctiva prior to incising. Prior to making the incisions depicted in FIG. 6A, the conjunctiva 602 is rotated relative to the sclera 604 from a rested position to a rotated position, such as through use of a finger or a clamp. An incision is made into the conjunctiva 602 and the sclera 604 to reach underlying structure and tissue, such as the trabecular meshwork 606 and the limbus 608. Following treatment of the underlying structure and tissue 606, 608, the treatment probe is retracted through the incisions in the conjunctiva 602 and the sclera 604, and the conjunctiva 602 is released. Upon release, the conjunctiva returns to its rested position, as depicted in FIG. 6B. Such movement of the conjunctiva 602 staggers the incision point from the incision point in the sclera 604 resulting in improved healing through improved blood flow and coverage of the sclera 604 incision by undamaged conjunctiva 602 tissue.

Figure 7:
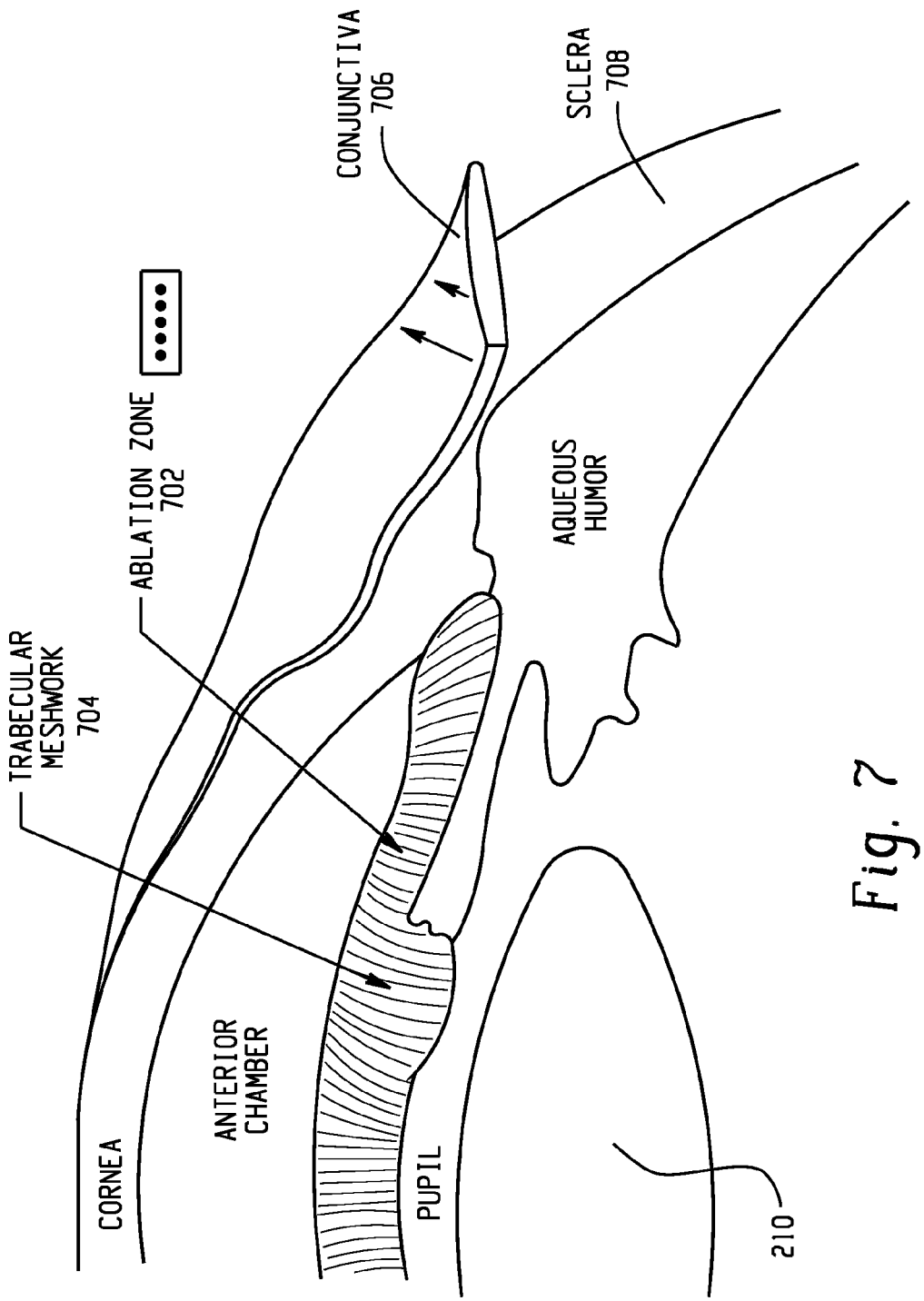
FIG. 7 is a diagram depicting a pattern of trabecular meshwork ablation that results in the generation of a kerf or channel for the outflow of aqueous humor.
Figure 8:
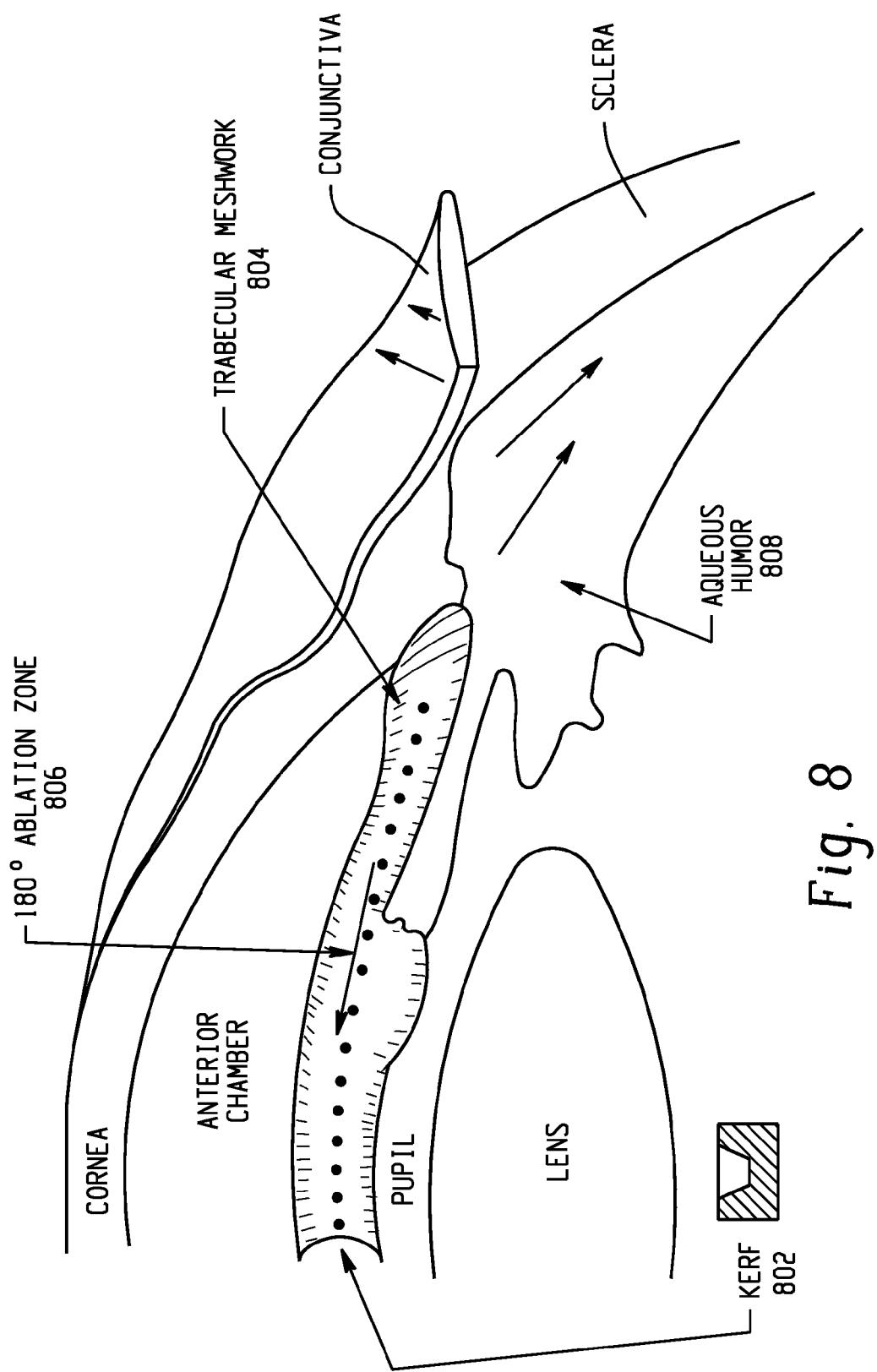
FIG. 8 is a diagram depicting the kerf or channel following ablation.

FIG. 7 is a diagram depicting a pattern of trabecular meshwork ablation that results in the generation of a kerf or channel for the outflow of aqueous humor. An ablation zone 702 of the trabecular meshwork 704 is accessed through a perpendicular incision in the conjunctiva 706 and the sclera 708. The trabecular meshwork 704 is ablated according to one or more instances of the dashed line pattern, shown at 710 to form a kerf or channel in the trabecular meshwork 704. FIG. 8 is a diagram depicting the kerf or channel following ablation. The one or more ablations according to the dashed line pattern depicted in FIG. 7 results in the kerf or channel 802 in the trabecular meshwork 804. Such a channel may span all or a portion of the circumference of the lens, such as a 180 degree ablation zone 806. The kerf of channel 802 in the trabecular meshwork 804 allows aqueous humor 808 to flow from the eye, reducing intraocular pressure in the eye.

Figure 9:
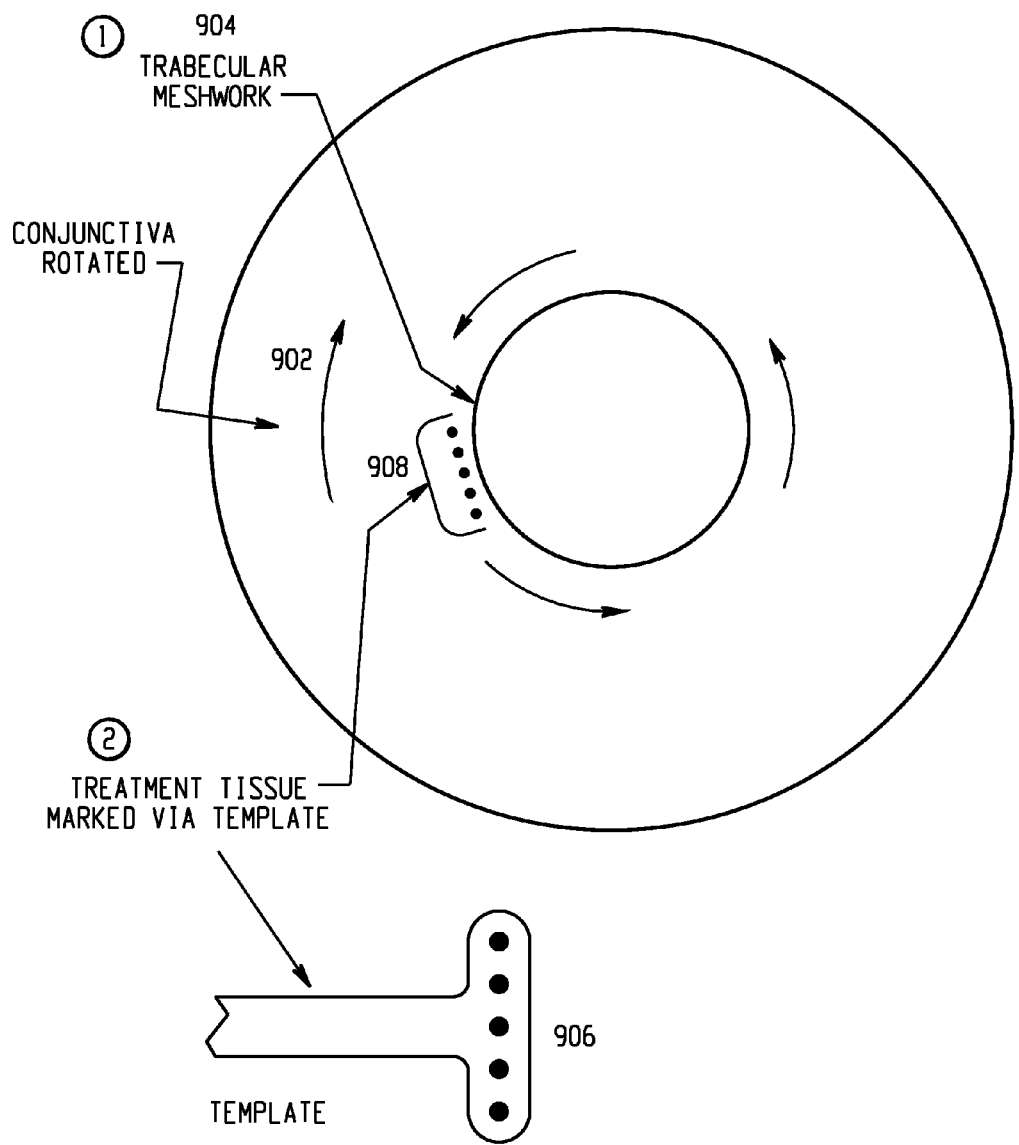
FIG. 9 depicts an example visible light pattern projected onto a trabecular meshwork of an eye to aid in ablation.

As noted above, incisions and ablations may be made according to predetermined patterns. To assist in accurate performance of such treatments, certain guides may be made available to the performer of such treatments to aid in precision and accuracy. In one example, light emitting diode (LED), low power laser pointer, or other visible light guides may be projected onto the eye to aid in treatment. For example, a desired location for a perpendicular or other incision (e.g., through a conjunctiva or sclera) may be projected onto the surface of the eye by a visible light pattern generator. As another example, a desired ablation pattern identifying desired points of ablation in a trabecular meshwork may be projected onto the trabecular meshwork by a visible light pattern generator. A laser tool or other cutting apparatus may then make incisions or ablations based on the projected visible light pattern, such as by making the incisions through lines in the visible light pattern. FIG. 9 depicts an example visible light pattern projected onto a trabecular meshwork of an eye to aid in ablation. The conjunctiva is rotated at 902 and the trabecular meshwork is accessed at 904, such as via a perpendicular incision through the conjunctiva. The trabecular meshwork to be treated is marked by a visible light template. The visible light template is depicted alone at 906, and the projection of the visible light template on the trabecular meshwork is depicted at 908. Having the template projected on the trabecular meshwork at 908, a technician can access the trabecular meshwork through the perpendicular incision and ablate the trabecular meshwork at the points noted in the projected pattern, such as via a bendable laser tip of a laser tool.

Figure 10A:
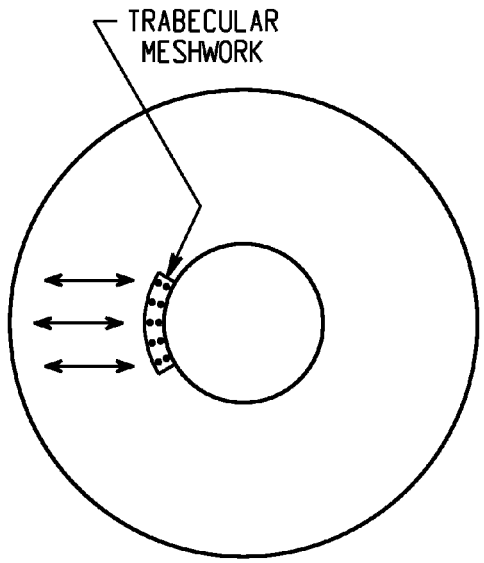
FIGS. 10 and 11 depict additional ablation patterns for a trabecular meshwork.
Figure 10B:
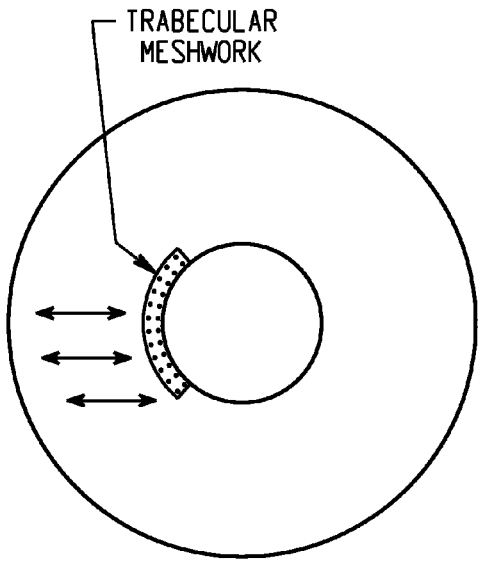
Figure 10C:
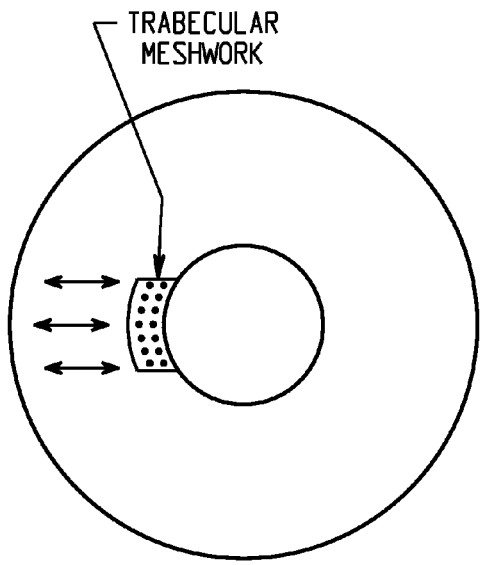
Figure 10D:
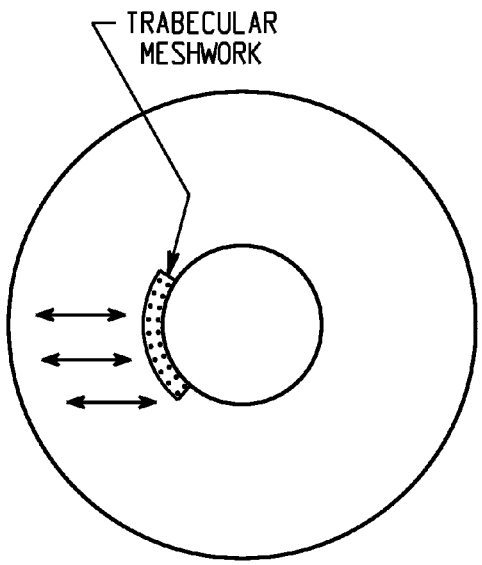
Figure 11:
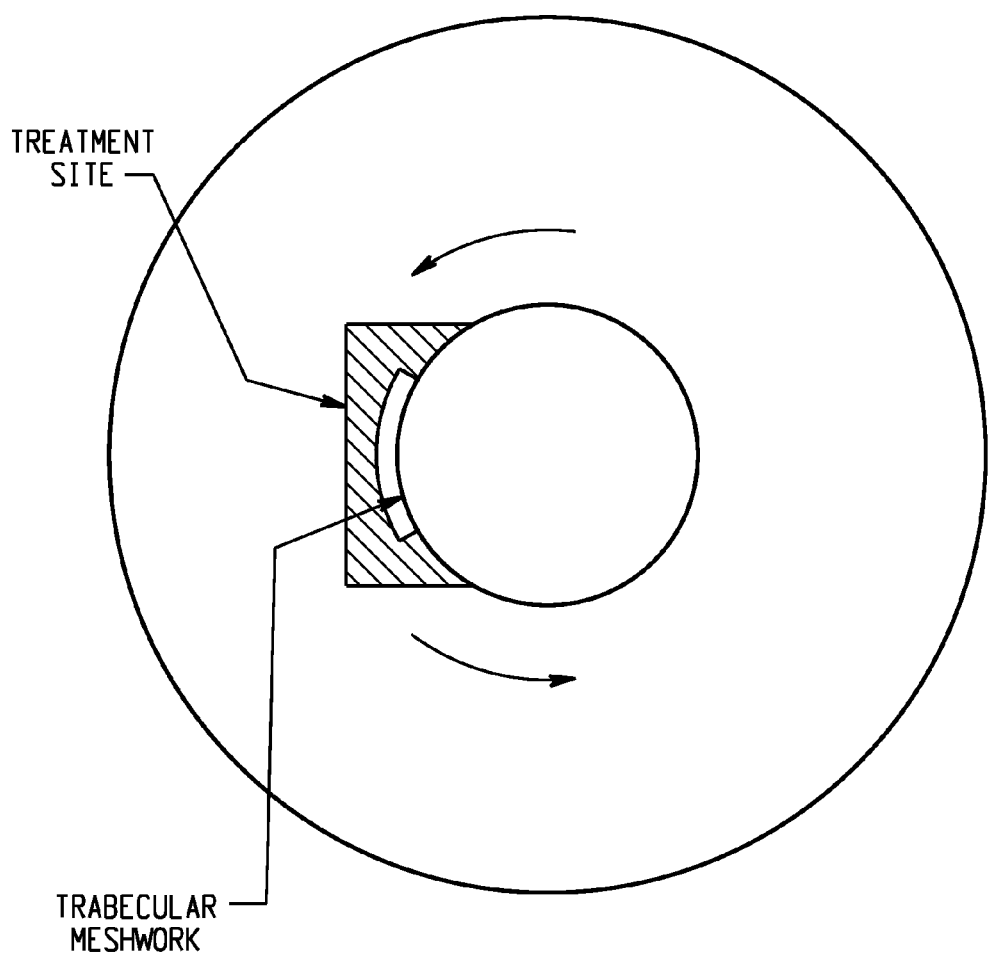

FIGS. 10 and 11 depict additional ablation patterns for a trabecular meshwork. Such patterns may be ablated by hand with the aid of a projected visible light pattern, substantially simultaneously using a laser tip tool configured to ablate a pattern in a trabecular meshwork, or using a computer-controlled scanning ablation tool. The pattern of FIG. 10a includes a single row of mid-size ablation points. The pattern of FIG. 10b includes multiple rows of small-size ablation points. The pattern of FIG. 10c includes multiple rows of large-size ablation points. The pattern of FIG. 10d includes multiple rows of mid-size ablation points.

An ablation pattern may be selected based on a number of factors, such as a current condition of an eye. If an intraocular pressure of an eye is substantially higher than normal, it may be important to quickly affect the flow of aqueous humor to reduce the intraocular pressure. In such a case, several large-size ablation points, as depicted in FIG. 10c may be desirable. In more extreme cases, where intraocular pressure is very substantially higher than normal, a pattern, such as the pattern depicted in FIG. 11, where substantially all of a section of trabecular meshwork is ablated may be utilized to result in immediate flow of aqueous humor from the eye. In contrast, where an intraocular pressure of an eye is only slightly above normal, a smaller number of smaller-bore ablations may affect the needed amount of aqueous humor flow without risks of more substantial flow such as prolapsed and soft eye.

Figure 12:
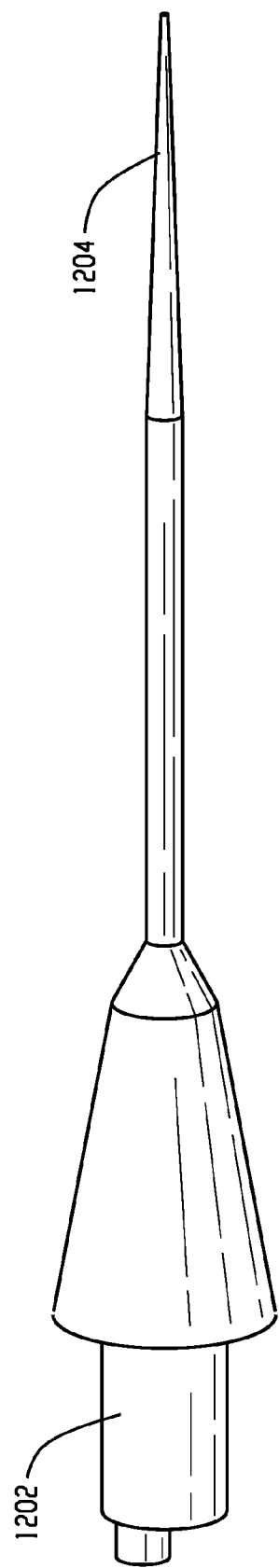
FIG. 12 depicts an example laser tool that includes a flexible tip.

FIG. 12 depicts an example laser tool that includes a flexible tip. The laser tool receives light energy at a first end 1202 and propagates the light energy along a length of the tool for focusing through a flexible tip 1204 at a second end. A flexible tip 1204 enables ablation of substantial portions of the trabecular meshwork through a single perpendicular incision without a need to transit the tip or any tool structure across the lens portion of the eye. The flexible tip 1204 may take a variety of forms, such as an end-firing flat, pointed, or curved tip or a side firing or radial tip. For example, the flexible tip may have a radial or side firing tip, such as is disclosed in U.S. Pat. No. 7,702,196, the entirety of which is herein incorporated by reference. Example flexible tips can further include the Perio 300 tip by BioLase, Inc., Part Number 740020. This tip has Twist-on convenience and eliminates time-consuming stripping and cleaving. This tip is bendable for access to all areas of the eye and can be used as a single use tip. The Perio 300 tip has a diameter of 1.1 mm and a fiber length of 7 mm or 9 mm with an outer tube length of 15 mm.

The exact details of a procedure within the context of this disclosure may take a variety of forms. For instance, according to certain implementations, relatively small perforations ranging from about 1 micron to about 1000 microns may be created with, for example, a micro-drill, laser, or needle. In other instances, alternative or additional tissue treatments (e.g., micro-apertures having spot shapes) may be either similarly formed in the tissue surrounding the trabecular meshwork or formed using means different from that used to form the mentioned tissue treatments, in the same or different locations, at the same or other points in time, and/or with the same or different sizes.

In modified embodiments, any of the tissue treatments may have sizes (e.g., maximum diameters) the same as or smaller than about 1 micron and/or larger than about 5 microns (e.g., ranging up to about 50 microns, or up to about 1000 microns, or more, in certain implementations). It may be observed that, and/or measures may be taken to attenuate or avoid a possibility that, with very small diameters (e.g., about 1 micron to about 1000 microns) walls of the perforations may tend to collapse on themselves. Laser characteristics can be adjusted according, for example, to a depth and diameter of desired cuts. For example, apertures formed with depths of a few microns may be generated with relatively high power densities and/or may have relatively small diameters.

Micro-apertures may be formed in the tissue surrounding the trabecular meshwork, for example, directing relatively unfocused treatment energy through the conjunctiva or sclera with a focal point of the treatment energy being targeted on the tissue surrounding the trabecular meshwork, or they may be generated endoscopically. According to certain implementations, the focal point can be moved (e.g., advanced distally in a direction toward the tissue surrounding the trabecular meshwork) as the depth of the cut increases into the tissue surrounding the trabecular meshwork, in which case conically-shaped apertures may result, as just one example, which exemplary formations may be beneficial in certain cases. In modified embodiments, micro-apertures may be formed in the tissue surrounding the trabecular meshwork endoscopically. Endoscopic access may be achieved through, for example, the ocular tissue surrounding the trabecular meshwork. Entry also can be accomplished, for example, adjacent to or about 1 mm from the Schlemm's canal.

In certain implementations, micro-apertures may be formed in the tissue surrounding the trabecular meshwork adjunctive to, for example, a glaucoma disease treatment procedure, which may involve, for example, formation of tissue treatments in the tissue surrounding the trabecular meshwork as described herein. The tissue treatments (e.g., micro-apertures in the tissue surrounding the trabecular meshwork) also may be treated to affect at least one property of the tissue of the tissue treatment. Removal of the tissue surrounding the trabecular meshwork may, for example, augment the flow of aqueous humor and accordingly enhance fluidics of the eye.

Low-level laser or light therapy or biostimulation of one or more parts of the eye (e.g., the tissue surrounding the orbit), further, may be performed to rejuvenate tissues thereof. In a case of the tissue surrounding the trabecular meshwork, a sebaceous liquid, for example, of the tissue surrounding the orbit may be increased to thereby enhance the stimulation of the aqueous humor. In such instances, the trabecular meshwork can be considered a target chromoform (i.e., target tissue). Generally, a wavelength of applied light energy can be aligned with a tissue type of the trabecular meshwork.

A type of low-level laser or light therapy or photo dynamic therapy (PDT) may be used, as another example, on or in a vicinity of (e.g., on tissue adjacent to) the trabecular meshwork to rejuvenate the circulation and thereby facilitate, for example, a clear tear formation in the eye. Light wavelengths of, for example, 670, 795, 819 and 980 nm may be employed in typical embodiments. A variety of light sources may be used, including low-level lasers and light-emitting diodes (LEDs). Continuous-wave (CW) energy or pulsed energy having a relatively high peak energy may be useful in such glaucoma disease treatments. The tissue surrounding the trabecular meshwork may be stimulated in some cases with, for example, CW energy gated, for example, on for about 200 ms and off for about 200 ms. The stimulation may restore the flow of aqueous humor to a flow into the drainage canal. The above low-level applications may also be applied to surrounding tissues according to modified embodiments, such as, for example, low-level laser therapy being applied.

Scanning can be performed with for example a relatively small spot size. A joystick may be provided to facilitate any of the scanning implementations described herein. In other instances, a larger spot size can be used without scanning. Low-level light therapy may be beneficially applied to treatment of a larger portion (e.g., a relatively large or entire area) of the surrounding tissue. Treatment power densities may be relatively low, being similar, for example, to power densities used in treatments of, e.g., tennis elbow, temporomandibular joint (TMJ), or tendonitis, and in representative embodiments having characteristics less than the following: a power density at the surface of the tissue being treated of about 1.47 W/cm$^2$, a power density within the tissue of about 0.39 W/cm$^2$, a dose of energy of about 23.6 J/cm$^2$ (for a 60 second laser exposure), and/or an energy of about 9 J within and about 33.5 J at the surface of the tissue being treated.

In one implementation, a type of low-level laser or light therapy or photo dynamic therapy (PDT) may be used to increase the efficacy of or stimulate the tissue in Schlemm's canal thus increasing the flow of aqueous humor. Entry may be through the conjunctiva and sclera or surrounding area using an endoscopic laser. An anterior insertion or posterior site can be lased to cause a more direct effect on the trabecular meshwork. One procedure may comprise lasing the trabecular meshwork (e.g., a portion of the surrounding tissue that allows the flow of aqueous humor) in order to make clear tears produce with the appropriate amount of circulation. According to one embodiment, the trabecular meshwork or surrounding tissue can be stained, making them a target chromoform, thereby resulting in selective treatment of the trabecular meshwork when exposed to optical energy.

One or more of the tissue treatments may be implemented as described herein using various forms of treatment energy, such as one or more of electromagnetic radiation (e.g., ablating optical energy, thermal optical energy, low level therapeutic optical energy, or radio frequency energy), ultrasound, and magnetism, alone or in combination with acupuncture or other therapeutic interventions. Embodiments may employ, as examples, laser acupuncture, light acupuncture, laser/RF acupuncture, and the like, separately and/or together in space and/or in time. In modified embodiments, any one or more of the tissue treatments described herein may be formed with a cutting or piercing tool, such as a needle or scalpel, alone or in combination with (e.g., in space and/or time) any of the aforementioned tissue-treatment generating implements. Typically, acupuncture may be performed once a meridian or trigger point is identified. Magnets and/or magnetism applied (e.g., separately and/or together in space and/or in time) in conjunction with the herein discussed techniques and/or ultrasound, may be beneficial as well. In particular, tissue rejuvenation may employ ultrasound, RF, laser, light, and/or magnets applied individually and/or in combination in space and/or time. Ultrasound applied to the eye, e.g., by varying a frequency of the ultrasound applied to eye tissue, may serve to recondition the eye.

Tissue treatments can be introduced into the trabecular meshwork or surrounding tissue. In exemplary implementations, each of the tissue treatments comprises a shape, which may resembles a dot, spot, a short dash, or other object. That is, the shape may in certain embodiments not take a form of an elongated arc or a spot. For instance, a maximum length dimension of a tissue treatment can range from about 0.01 mm to about 10 cm, a maximum width dimension can range from about 0.01 mm to about 10 cm, and a maximum depth dimension can range from about 0.01 mm up to about 10 cm (or, alternatively, up to about 115 cm). The shapes and locations may be dependent on the "mapping" of the surrounding tissue wherein, for example, there are dense locations depicted by the trabecular meshwork or surrounding tissues. The eye muscles and critical eye structures may also play a role in determining shapes and/or locations of the tissue treatments that may be required. The thermal properties of the energy injected into the tissue may require protection to eye muscles and critical eye structures.

In certain embodiments, tissue treatments may be formed to have maximum diameters of about 1 micron to about 10 cm, and in particular implementations having maximum diameters of about 20 microns to about 20 cm. In other implementations, which may or may not consist of or comprise the application of ablating optical energy to the trabecular meshwork, other definitions or meanings for the term "tissue treatments" may apply.

One or more of the tissue treatments may be implemented using various forms of treatment energy, such as one or more of electromagnetic radiation (e.g., ablating optical energy, thermal optical energy, low level therapeutic optical energy, or radio frequency energy), ultrasound, and magnetic implementations.

Regarding formation of tissue treatments using treatment energies, typical systems for providing treatment energies may comprise one or more of an electromagnetic source such as a laser (e.g., a diode laser) having a predetermined wavelength, an ultrasound device with a predetermined pulse, a heat emitting device with a pre-determined setting that interacts with desired parts of the eye to form tissue treatments, a radiofrequency module, an ultrasonic component, and combinations thereof. Electromagnetic energy devices may comprise, for example, lasers having all wavelengths, such as lasers having wavelengths ranging, for example, from about 0.15 microns to about 3.2 microns. Exemplary laser beam spot sizes can range from about 0.001 mm up to about 10 cm (or, alternatively, up to about 20 cm), and exemplary laser energy per pulse values can range from about 0.1 mJ to about 50 mJ depending on, for example, the pulse duration and the laser beam spot size. Typical pulse laser widths may range from about 100 nanoseconds to about 1000 microseconds. Another laser that can be utilized is the diode laser with the wavelength from 810 nm to 980 nm and energy from 0.1 watt to 10 watts in either continuous or pulsed mode.

Particular implementations of lasers for use on, for example, the treatment utility may comprise Er:YAG, Er:YSGG, Er, Cr:YSGG, or CTE:YAG lasers operated at exemplary wavelengths ranging from about 2.69 microns to about 2.8 microns, and about 2.94 microns; XeCl excimer lasers operated at an exemplary wavelength of about 308 nm; frequency-shifted solid state lasers operated at exemplary wavelengths of about 0.15 microns to about 3.2 microns; excimer lasers of ArF operated at an exemplary wavelength of about 93 nm; harmonic generations of Nd:YAG or Nd:YAL or Ti:sapphire lasers operated at exemplary wavelengths of about 190 nm to about 220 nm; CO lasers operated at a wavelength of, for example, about 6.0 microns and carbon dioxide lasers operated at a wavelength of, for example, about 10.6 microns; diode lasers operated at exemplary wavelengths of about 0.8 microns to about 2.1 microns; gas lasers operated at exemplary wavelengths of about 2.6 microns to about 3.2 microns; and other gas or solid state lasers including flash-lamp and diode-laser pumped lasers operated at exemplary wavelengths of about 0.5 microns to about 10.6 microns; and optical parametric oscillation (OPO) lasers operated at exemplary wavelengths of about 2.6 microns to about 3.2 microns.

According to exemplary implementations of applying energy (e.g., optical energy) to tissues (e.g., the tissue surrounding the trabecular meshwork or trabecular meshwork), any of the phrases "plurality of tissue treatments," "tissue treatments," "treatments," "tissue treatments" or "markings" can in certain embodiments refer to tissue treatment groupings and/or tissue treatment markings corresponding to tissue treatment groupings. Any of these phrases can, in the same exemplary implementations and embodiments or in others, refer to two or more tissue treatments arranged in a non-linear and non-arcuate grouping (e.g., pattern) on the tissue, and/or arranged in a plurality of non-linear and non-arcuate groupings (e.g., patterns) on the tissue. Tissue treatments or groupings of tissue treatments may comprise random spot shapes, (straight, curved, or otherwise), or may comprise spot shapes (straight, curved, or otherwise) formed in a pattern that is pre-determined based on a treatment customized to an area.

In other implementations, which may or may not consist of or comprise the application of ablating optical energy to the trabecular meshwork, other definitions or meanings may apply. Typical embodiments can comprise grid-like groupings of tissue treatments, wherein for example the individual tissue treatments can be arranged in rows and columns in a staggered or non-staggered fashion. Other typical embodiments can comprise grid-like groupings, and/or other uniform or substantially uniform groupings, of tissue treatments. Still further embodiments can comprise non-uniform groupings of tissue treatments. The groupings may be formed manually and/or with the aid of automated devices such as computer controlled or aided scanners.

Regarding formation by manual means, an output, such as, for example, a fiber optic tip in cases where the treatment is electromagnetic energy, may be used to focus electromagnetic (e.g., optical) energy onto for example the trabecular meshwork and/or tissue surrounding the trabecular meshwork in order to form tissue treatments to depths of, for example, about 1% to about 99% of the trabecular meshwork. An exemplary implementation can comprise an Er, Cr:YSGG laser with a 200 micron quartz or sapphire (contact) tip operated at 1.25 W and 2.78 microns, wherein for example incisions may expand up to 2 mm width after laser energy is imparted with exemplary lengths of incision being about 4 mm. In other embodiments, a surgical scalpel (e.g., diamond blade) may be used to form tissue treatments having depths as previously discussed in connection with fiber optic tip embodiments. In further embodiments, plasma technology can be used.

Regarding formation by automated scanning, typical optical systems for providing treatment energies may comprise ablative lasers having predetermined wavelengths and being focused by, for example, a tissue surrounding the trabecular meshwork which is directed, for example, onto a scanner for patterning (e.g., using a mirror) onto the patient's eye. The scanner may comprise motorized mirrors and/or a refractive optical means such that laser energy is delivered (e.g., scanned) to the eye in predetermined patterns. The scanner thus can automatically direct laser energy over, for example, the trabecular meshwork or the tissue surrounding the trabecular meshwork of the eye to generate predetermined patterns and thereby form tissue treatments to depths of, for example, about 1% to about 99% of the trabecular meshwork. Operating parameters for the laser can be 0.01 watts to 10.0 watts with a repetition rate of 0 to 100 Hz. Cautery device parameters can be technique specific, and can depend upon the use and desired application. Furthermore, the output can vary depending upon the manufacturer of the cautery device.

One or more of various advantages may be realized through implementations of scanners in the context of many of the presently described embodiments, such advantages including precision, repeatability, predictability of results, uniformity of tissue treatment sizes and/or shapes, uniformity of spacings between and/or relative positions of tissue treatments, and speed. Moreover, scanners may be implemented to determine surface topographies and thicknesses of various layers of the eye, as known to those skilled in the art. In addition, embodiments implementing scanners may further provide a benefit of modifiability of treatments to a given patient. For instance a grouping or groupings may be formed during only a single procedure on the patient's eye (e.g., one surgical procedure during one patient visit) and, subsequently, should a need be presented, one or more follow-up procedures (e.g., implemented over multiple patient visits) may be performed on the patient's eye. These procedures may be performed in any order and/or any sequence of sub groupings, may be implemented.

Precision and efficacy of tissue treatments may be enhanced when the depth or depths of the tissue(s) being affected (e.g., depth into trabecular meshwork) is/are accurately determined and controlled. In the contexts of manual generation of tissue treatments, a surgeon may observe a color change of, for example, the tissue surrounding the trabecular meshwork being treated to determine when the tissue-treatment depth reaches a desired level. In the context of procedures on the tissue surrounding the trabecular meshwork, the surgeon may, for example, cease the forming or cutting of a tissue treatment when a color change to dark (which may be more pronounced in the context of optical ablating rather than scalpel cutting) begins to change at the bottom of the tissue treatment being formed. A darkening of hue (e.g., to a dark brown) as tissue is affected (e.g., removed) at the bottom of the tissue treatment may indicate, for example, less remaining trabecular meshwork and a greater exposure of the underlying layer (e.g., the vascularized tissue surrounding the trabecular meshwork), at which time the surgeon may decide to slow or stop altogether formation of that tissue treatment or to stop formation altogether.

When scanners or other automated or semi-automated systems are used in connection with generation of tissue treatments, the patient's trabecular meshwork thickness can be measured, for example, pre-operatively and the tissue-treatment depth controlled accordingly. In representative implementations, a scanning laser, or any other known tissue layer thickness measuring device, can be used to determine and subsequently control this depth. For example, the scanning laser may work with another optical or ultrasound device to detect the depth. Magnetic devices also may be used to the same purpose. As another alternative, a sensor may determine depth by automatically detecting, for example, a change in hue while lasing. Generally, a device such as, e.g., an optical detector, a colorimeter, an ultrasound probe, a device for generating and detecting electric and magnetic fields, and a tonometer can be used to measure depth of cut. Other methods of depth estimating include monitoring a bottom of a kerf or other topography while looking for bulging. Temperature changes also may provide an indication of depth, with a drastic change in temperature being an indication that an endpoint of the incision or kerf has been reached.

In some embodiments, a camera, such as, for example, an intraocular fiber optic camera may be incorporated. The camera may be used, for example, to provide optical aid in conjunction with the operating site and/or to provide, for example, a determination of the incision depth in relation to the tissue surrounding the trabecular meshwork. A change of color in the ocular structure, for example, can facilitate a determination of when the incisional appropriate penetration level has been reached. In other embodiments, the camera (e.g., intraocular or extraocular) may be configured to facilitate viewing of tissue-treatment formations, real-time or post-procedure, or to facilitate automated or semi-automated control of, for example, a procedure for forming tissue treatments. A real-time viewing example may comprise, for example, use of an intraocular camera to facilitate real-time sub-trabecular meshwork visualization during formation of tissue treatments (e.g., via laser ablation) in the trabecular meshwork. While monitoring the formation of a tissue-treatment using a camera, a change in color may be automatically detected and/or visually detected by a user.

In exemplary embodiments, the camera may be secured, for example, to an output tip of a system (e.g., a laser system), which provides treatment energy through a fiber optic tip. The output tip can comprise barbs for facilitating insertion of the output tip through the tissue surrounding the trabecular meshwork with relative ease but resisting removal of the barbed output tip from within the trabecular meshwork once inserted.

The fiber optic camera can be integrated into the handpiece or can branch from the output tip. Similar constructions can be implemented into an oval shaped output tip. Other similar constructions can comprise a fiber optic camera or fiber optic camera lens surrounding the fiber optic tip. According to any of the embodiments described herein, the camera may comprise a visualization fiber optic leading to a remotely disposed (e.g., not on the output tip) camera. The fiber optic may be disposed in a cannula, which further may contain one or more of a treatment-energy waveguide (e.g., a fiber optic tip), a visualization light source, a fluid output and an aspiration source (e.g., a calibrated aspiration source). Fluids, such as liquids (e.g., water) and/or air, can be directed over a lens of the intraocular camera and/or across a field of view of the intraocular camera to create a better viewing area and/or aspiration can be applied for removing fluids from a vicinity of the lens or field of view. In addition to or as an alternative to the discussed fluid and aspiration structures and techniques for use in combination with, for example, an intraocular camera lens, water repelling coatings (e.g., Rain-X® Original Glass Treatment, made by SOPUS Products of Houston, Tx.) can be applied to the lens for enhanced visual clarity.

According to one embodiment, washing the output tip with water operates to clean the coated, or non-coated, intraocular camera lens. In output-tip washing or other lens cleaning embodiments and/or any other water (e.g., sterile water) embodiments described herein, a gelled water or viscoelastic gel (e.g., a viscous water based gel, such as Viscasil®, available at www.viscasil.com), which can be transparent, may be used alone or in combination with water or other fluids or liquids. Any of the mentioned embodiments implementing fluid (e.g., water) for lens cleaning may incorporate any of the methods and structures described herein for adding fluid (e.g., water).

Tonometric techniques of depth measurement may comprise measuring pressure at a plurality (e.g. three or four) of locations on the trabecular meshwork or surrounding tissues before a procedure is initiated. Pressure measured during the procedure then may be interpreted according to the initial pressure, with the interpretation providing an estimate of depth. A similar method may be applied to techniques for depth measurement using electric fields, magnetic fields, and chemical sensing. Mechanically, a Q-tip multi-wavelength laser device may be employed to detect depth at a bottom of a cut. For example, one wavelength (i.e., color) may indicate depth; another color may indicate vascularization related to cancer growth. Black light may be useful in identifying whites, so one approach is to continue cutting until whites can no longer be seen. In other embodiments, a UV light may be placed for ease of use in determining the area to be treated while viewing the appropriate depth. Alternatively, if a wavelength is chosen that makes blue visible, then cutting may continue until a blue hue is observed. Summarizing, different wavelengths of light may be sensitive to different characteristics of, for example, the trabecular meshwork. These differing sensitivities may be exploited to determine a condition of a tissue being treated (e.g., the trabecular meshwork) during a procedure, the condition being different at different layers of tissue.

Alternatively, a doctor may form a test perforation through the ocular surrounding tissue and into the trabecular meshwork (i.e. extract a core sample), the test providing an indication of circulation, and depth of the trabecular meshwork. This indication may be used to determine and refine a treatment procedure (i.e. type of ablation, number of ablations, their locations and depths). The amount of tissue in the trabecular meshwork may relate to the ability of the treatment to perform consistently. Granular tissue in the tissue surrounding the trabecular meshwork may relate to the trabecular meshwork while colors may aid in identifying components of the tissue surrounding the trabecular meshwork. A combination of the above tools including, in one example, an olfactory detector (e.g., sniffer), can be used to determine locations and appropriate times for performing a procedure. In certain embodiments, applied in addition to as an alternative to any of the above features, patterns of tissue treatments can be determined by a device, which can mark and/or apply the tissue treatments in areas based upon a circulation theory wherein the tissue treatments are imparted into the trabecular meshwork (using, e.g., a scanning laser) in the determined areas.

In addition to pre-operative measurements of depths of the layer or layers being affected, depths of remaining tissue layers at the bottoms of tissue treatments may be measured during formation of the tissue treatments (e.g., in real-time), with one or more operating parameters such as remaining tissue-treatment formation (e.g., cutting) time, pulse width, repetition rate, average power, coolant, etc., being adjusted in accordance with the results of the real-time depth measurement. For instance, a pre-operative scanning measurement may determine the trabecular meshwork to be about 700 microns, and ½ second into the formation of a tissue treatment a real-time depth measurement may indicate a remaining depth of the trabecular meshwork at the bottom of the tissue treatment being formed to be about 325 microns. It may be determined (e.g., automatically determined) at that time to continue formation of the tissue treatment for another ½ second. This iterative process may be repeated, wherein for example a subsequent real-time measurement of remaining-depth of about 100 microns may be detected ¼ second later thus triggering, for example, a decision to continue formation for another ⅛ second. Various combinations and implementations of depth analysis, cutting type, speed control, and feedback algorithms, among other parameters, may be implemented in various combinations, for monitoring and controlling tissue-treatment formation depths and formation characteristics, for obtaining, among other things, one or more of greater monitoring control and tissue-treatment formation accuracy. For example, the laser may have a tip of 200 microns and enter the "treatment tissue" to a predetermined depth as seen by ultrasound technology, Artemis technology, confocal microscopy, tonometry, laser, or UV light. The power will be in the range of 0.01 watts and the repetition rate of 10 Hz, but will vary with other manufacturer specifications for their device.

Also, when scanners are used, initial steps comprising, for example, determining one or more reference points of the eye (e.g., a center of the pupil, one or more points on the patient's retina, triangulated unique points on the patient's iris, and/or tissue treatments or other markings formed on the patient's eye at an early stage of a procedure for the purpose of, for example, those tissue treatments being used as reference points) may be implemented so that locations of tissue treatments may be defined and/or recorded relative to the one or more reference points for use during the initial formation of the tissue treatments and/or for use during follow-up procedure(s) wherein tissue treatments may be modified and/or additional tissue treatments may be formed. In accordance with one aspect, tissue treatments formed during an initial or earlier procedure are used as reference points during remaining steps of the initial procedure and/or for the forming of additional tissue treatments during follow-up procedures. For example, density mapping may be implemented wherein ultrasound is used to facilitate detection of tissue features such as a surface topography (e.g., locations of previously formed trabecular meshwork) for use as reference points. Also, depths of previously formed tissue treatments may be detected to provide an option of, for example, augmenting depths of one or more tissue treatments according to desired protocols. A topography unit will map the tissue surrounding the trabecular meshwork and form a grid. The grid will be placed over the eye with the "tissue treatment" sites marked and then lased or treated by a method of removing aqueous humor obstruction.

According to an example, ablating optical energy can be focused using optics into the trabecular meshwork so that a peak concentration of the ablating optical energy occurs within the trabecular meshwork and a concentration of the optical energy in the tissue surrounding the trabecular meshwork is substantially lower or, in one embodiment, below an ablation threshold. Dye enhancing the tissue to be treated can be used, for example, to facilitate one or more of assuring that the treatment energy (e.g., laser energy) penetrates the desired area wherein different colors of dye may be used, assuring that the treatment energy (e.g., laser energy) penetrates to the appropriate pre-determined depth wherein different consistencies and colorations can be used to this end, and allowing for better viewing of the treatment area wherein dyes can be used in conjunction with the appropriate light source for "high lighting" and the background light can be reduced for enhancement. For example, the trabecular meshwork can be stained with yellow dye allowing for the location of diseased aqueous humor (e.g., clogged trabecular meshwork) to be highlighted a darker yellow. In general, regarding dye enhancing of the tissue to be treated, dyes may typically be red, green or dark in nature and can be used to enhance the depth, length or width of the incision of the tissue to be treated. Such methods typically may be combined with treatment energies such as infrared energy. The operating parameter can vary depending on the type of enhancement used, type of tissue, desired depth, length and width, and the spectrum of energy used. Thus, in the context of, for instance, the preceding example, the term "non-invasively" should be interpreted to mean that portions of the trabecular meshwork and surrounding tissues penetrated by the treatment energy are not substantially affected (e.g., not ablated), or are affected to a lesser extent than that to which the underlying ocular tissue is affected, by the treatment energy.

As used herein, and not merely in the context of the present example, the term "invasively" should be interpreted to mean that portions of the tissue (e.g., trabecular meshwork and or any other tissues) penetrated by the treatment energy are substantially affected (e.g., ablated) by the treatment energy. Invasive penetration of tissue by treatment energy may generate, for example, a tissue treatment.

In other examples, one or more of the tissue treatments can be applied to penetrate through the tissue surrounding the trabecular meshwork (e.g., to invasively penetrate wherein penetrated portions of the tissue surrounding the trabecular meshwork are affected, such as by being ablated) and to treat (e.g., ablate) the trabecular meshwork. According to a particular implementation, a collimated beam of ablating optical energy may be directed through both the tissue surrounding the trabecular meshwork and through, for example, a majority or more of the thickness of the trabecular meshwork, whereby tissues of both the tissue surrounding the trabecular meshwork and trabecular meshwork is ablated along the path of the collimated beam. The parameter ranges can, in exemplary embodiments, be dependent upon desired, predetermined or expected wavelengths, lengths, widths and/or heights of incisions, and exemplary tissue parameters/types to be affected can include tissue surrounding the trabecular meshwork and trabecular meshwork. In certain implementations, the treatment energy beam can be shaped in the form of a complete tissue treatment (e.g., elongated kerf). A mapping can determine the location, pattern, shape and landscape of the region acquiring the treatment based on density. The treatment energy beam can be completed by contact or non-contact of the laser energy in a pulse mode, or continuous mode that is proximal to the treatment area using a fiber based or scanner based delivery system with a predetermined software pattern or template. A beam splitter may be used to disperse energy of the beam in a pattern of the treatment area.

Dye-enhancing the tissue to be treated can, for example, be implemented. Dyes can comprise, for example, red, green or other relatively dark colors and can be used to enhance (e.g., selectively enhance by application to certain areas and/or selective coupling or matching of laser types to tissue and dye types) or otherwise affect the depth, length, width or other characteristic of the incision of the tissue to be treated. For instance, an area can be dyed for pretreatment with a laser having a wavelength that is substantially or highly absorbed by blood, wherein following (or during) the dying the heating laser energy can be directed over the dyed tissue treatment areas to cause heat or to otherwise affect a propensity of such tissue treatment areas to bleed during subsequent formation of the tissue treatments. In certain embodiments, the tissue treatment markings themselves may be formed as the dyed areas. In other embodiments, the depth, length, width or other characteristic of the incision of the tissue to be treated can be contacted with energy from a laser having a wavelength that is substantially or highly absorbed by blood, wherein following (or during) the contacting the heating laser energy can be directed over the tissue treatment areas to cause heating or to otherwise affect a propensity of such tissue treatment areas to bleed during subsequent formation of the tissue treatments.

According to typical implementations, steps may be incorporated to ensure that pretreatment heating energy or subsequent ablating energy does not adversely affect the retina or other tissues. Such implementations may embody one or more of relatively low energy levels, tissues-type and/or color (using, e.g., dyes) matching with relatively high-absorption wavelengths (e.g., Nd:YAG or Er, Cr:YSGG), and focusing of the energies well in front of the retina. The energy can range from 0.1 watt to 40 watts. The laser can also be a femtosecond. The energy will penetrate through the conjunctive, to the sclera and ablate the trabecular meshwork. Dye enhancements can be applied to the desired treatment area allowing only that area to be treated and allowing the structures that are not matching the absorption wavelengths to be not affected by heat or energy from the treatment area.

Any one or more of the preceding methods may be practiced or combined with, for example, application of infrared energy as the treatment-energy, wherein, again, operating parameters can vary depending on one or more of the desired type of enhancement, such as irrigation, aspiration, type of tissue, depth, length, width, other characteristic, and spectrum of energy used.

A dimension (e.g., a cross-sectional shape or area measured in a direction transverse to a direction of propagation of the treatment energy) of a tissue treatment may remain relatively constant through a depth of tissue (e.g., the tissue surrounding the trabecular meshwork and/or trabecular meshwork) or may change with depth. For example, one or more tissue treatments may be formed to have cross-sectional shapes or areas that decrease (or, alternatively, increase) with depth into the trabecular meshwork, such as would be the case, for example, with a circular tissue treatment having a diameter that decreases with increasing depth into the trabecular meshwork. This enhancement may help the user ensure that a perforation does not occur (since the treatment diameter decreases) and lead to hypotony or soft eye. In typical implementations, a tissue treatment (e.g., a conically-shaped tissue treatment according to the preceding example) may comprise, for example, a diameter that tapers from about 0.1 to about 100 percent with each 1 percent drop in depth. In a particular example, the diameter may drop by about 1 percent for each 1 to 20 percent drop in depth. In the context of, for example, a tissue implant (e.g., a conically-shaped tissue implant) being formed in the trabecular meshwork, by way of treatment energy being directed non-invasively through the tissue surrounding the trabecular meshwork, a tissue implant dimension (e.g., diameter) may taper within the trabecular meshwork from about 1 to about 100 percent with each 1 percent drop in depth and, in a particular example, may drop by about 1 to about 20 percent for each 1 percent drop in depth within the trabecular meshwork.

The conjunctiva is approximately 1 mm, the sclera can be up to 3 mm, and the trabecular meshwork is approximately 2 mm in depth, but only 0.5 mm thick depending on the health of the tissue. The more diseased, the thicker the trabecular meshwork will be. Removed or affected areas corresponding to tissue treatments may for example be filled-in by a surgeon with any known biocompatable materials, such as, for example, Tisseal, anti-inflammatories or antibiotics. Removed or affected areas corresponding to tissue treatments are at least partially filled-in by the body (e.g., via the body's natural response) with sub-trabecular meshwork glandular tissue which may, for example, augment a property of the eye. For example, in the case of the trabecular meshwork, the new sub-trabecular tissue infiltrating a removed or affected area of the conjunctiva or sclera may have a greater elasticity or be more flexible than the original tissue surrounding the trabecular meshwork. The body's introduction of healthy aqueous humor into removed or affected areas thus may increase the flow of, for example, aqueous humor. In the example of removed or affected areas in the tissue surrounding the trabecular meshwork, new sub-glandular tissue in, for example, the trabecular meshwork may facilitate or enhance a functionality or other property of the underlying tissue surrounding the trabecular meshwork.

According to typical implementations, the trabecular meshwork may be treated by directing treatment energy through the over the tissue surrounding the trabecular meshwork with use of laser technology, whereby as previously mentioned the trabecular meshwork may be treated with treatment energy (e.g., laser energy) aimed (e.g., focused) in the tissue surrounding the trabecular meshwork, leaving the adjacent structures relatively undisrupted. For example, laser energy can be directed to focus or converge on the underlying trabecular meshwork wherein, for example, the laser energy has a relatively low power density (e.g., a large spot size) on the tissue surrounding the trabecular meshwork while at the same time having a relatively high power density (e.g., a relatively small spot size) on the underlying trabecular meshwork, and wherein the absorption rate is that of sclera and conjunctiva adjacent to the trabecular meshwork so that the laser energy forms a "v" in the trabecular meshwork that cuts only the trabecular meshwork tissue. The absorption rated is determined by the laser that is used and the tissue that is treated. For instance, the Er:YSGG looks for water, so the more aqueous the tissue, the less char and faster treatment time. One can add water to a relatively non-aqueous tissue on the surface so that the tissue is ablated faster.

The tissue surrounding the trabecular meshwork may be rotated or torqued from a different site at varying degrees in order to obtain, for example, better cosmetic effects (e.g., reduced reddening). Tissue treatments (e.g., kerfs) employed in such procedures may be formed in varying shapes as previously mentioned. Typical shapes can include, as examples, "u" and "v" shapes. The kerfs may also be made wherein the center of the kerf has more tissue than the edges. Generally, a kerf can have a width that varies according to different density factors and aqueous humor in different densities. However, incisional trabecular meshwork depths of tissue treatments in certain implementations remain constant. According to certain embodiments, an ultrasound unit can be used to remove both aqueous humor and target tissue. In other embodiments, cautery can be used, for example, to improve the clarity of the site where tissue treatments are to be formed and/or to generate the tissue treatments. Moreover, a light having a certain color, such as a black light, may be used to enhance a view of tissue surrounding the trabecular meshwork tissue in certain embodiments. Further, various colors may be placed in a scope (e.g., microscope) to enhance vision (e.g., surgeon discernment of features). For instance, green may allow a user to better see depth of penetration. Additionally, a tonometer may be used to detect pressure of a tissue treatment area, and/or a femtosecond laser can be used to remove or cut tissue of the tissue treatment.

One or more of the tissue treatments may be introduced with the adjacent structures in place, wherein for example the tissue surrounding the trabecular meshwork is left in a naturally-occurring orientation over the trabecular meshwork. In such embodiments, penetration paths through/into the trabecular meshwork, sclera and conjunctiva may be aligned or substantially aligned. For example, a beam of electromagnetic energy may be directed through both the undisturbed aqueous humor and through, for example, a majority or more of the thickness of the tissue surrounding the trabecular meshwork. The beam may travel through the tissue surrounding the trabecular meshwork in a non-invasive or invasive manner as described above, whereby, in the latter case for example, tissues of both the trabecular meshwork and tissue surrounding the trabecular meshwork may be ablated along the path of the beam of electromagnetic energy. This is illustrated in FIG. 8 and shows how the treatment tissue can be made into a kerf through the ablation zone. The insertion point lends itself to an area that can allow the user to insert the treatment method and extend it through the trabecular meshwork from a 180 degree method.

One or more of the tissue treatments described herein may be introduced with parts or substantially all of the tissue surrounding the trabecular meshwork altered (e.g., removed, reconfigured or repositioned such as by rotating the tissue, or separating and/or shifting the trabecular meshwork, relative to the aqueous humor) before or during introduction of the one or more of the tissue treatments, in any order or sequence of steps. Thus, with any of the implementations described herein, parts of the tissue surrounding the trabecular meshwork may, in certain embodiments, be manipulated while other parts are left in a naturally-occurring orientation over the trabecular meshwork. In other implementations, parts of the tissue surrounding the trabecular meshwork above portions of the sclera and conjunctiva receiving tissue treatments may be manipulated and/or other parts of the trabecular meshwork above portions of the sclera and conjunctiva receiving tissue treatments may be left in a naturally-occurring orientation over the trabecular meshwork. Furthermore, with any of the implementations described herein, substantially all of the trabecular meshwork may be reconfigured or repositioned relative to, for example, the tissue surrounding the trabecular meshwork.

Other aspects may comprise introducing one or more of the tissue treatments through the sclera and conjunctiva in one or more of the pre- or post-altered states of the aqueous humor. With respect to exemplary embodiments wherein the conjunctival and scleral tissue is repositioned before application of treatment energy and formation of tissue treatments, once the tissue surrounding the trabecular meshwork is brought to (or brought back to) assume (or at least to approximate) a naturally-occurring configuration or orientation (or is otherwise brought to a post-treatment configuration or orientation), some or all of the penetration paths through/into the trabecular meshwork and aqueous humor are not aligned. This lack of alignment between penetration paths of the tissue surrounding the trabecular meshwork and sclera, or alternatively the covering-up of penetration paths through the sclera and conjunctiva in embodiments wherein, for example, penetration paths are not formed in part or all of the tissue surrounding the trabecular meshwork, can serve to provide, for example, one or more of a sealing effect for enhanced healing and structural integrity to the affected layers.

With reference again to FIG. 1, one example of repositioning the tissue surrounding the trabecular meshwork can include rotating the tissue surrounding the trabecular meshwork, relative to the trabecular meshwork, before application of the tissue treatments. The tissue surrounding the trabecular meshwork can be gripped and rotated an amount, such as, for example about 1 to 2 degrees, or more broadly about 1 to 90 degrees, about the center point 36. In other implementations, the rotation may range from about 1 to about 45 degrees, or more, and/or different portions of the tissue surrounding the trabecular meshwork may be rotated, for example, at different points in time, in different directions and/or in different amounts. Considering FIG. 2 and FIG. 3, following such rotation, the tissue surrounding the trabecular meshwork may (or may not) be held in the rotated position, for example, while some or all of the tissue treatments are applied. After application of some or all of the tissue treatments, the tissue surrounding the trabecular meshwork can be moved back, to a full or partial extent, to its naturally-occurring orientation and/or can be released so that the tissue surrounding the trabecular meshwork moves, to a full or partial extent, back to its naturally-occurring orientation. FIG. 1 shows a treatment site where the energy will penetrate (e.g., through one treatment energy projection (i.e., one insertion point, or one spot, as shown in the blowup view)) through the conjunctiva and sclera onto the trabecular meshwork in a line pattern as the conjunctiva is rotated. FIG. 2 shows the second pattern that has the insertion point over the trabecular meshwork target tissue through the conjunctiva and sclera. The insertion point can be anywhere over the trabecular meshwork. The arrows in FIG. 2 show the rotation of the conjunctiva. FIG. 3 shows the ablation zone in the trabecular meshwork showing that the trabecular meshwork has been ablated in a tunneling fashion extending throughout.

A typical implementation of the ablation comprises cutting (e.g., slicing through, as distinguished from removing) of the fibers (e.g. 5-30% of the fibers) in such a manner (e.g. via thermal ablation so they do not heal back or reform) so as to facilitate the flow or better flow of aqueous humor. In this regard, a smaller spot size may promote faster or better healing without compromising the ablation/cutting effect of the treatment energy.

The insertion point for the energy to ablate the trabecular meshwork extends through the conjunctiva and sclera before proceeding into the trabecular meshwork. This can be completed in one pass or perhaps multiple passes depending on the size of the treatment energy and the unique nature of the individual's trabecular meshwork. The trabecular meshwork is ablated via treatment energy and represented by the white in FIG. 3 that was previously represented by black in FIG. 2. The arrows in the conjunctiva represent rotation of the conjunctiva prior to the application of treatment energy. FIG. 4 shows the completed ablation where the conjunctiva has been rotated back, and closure/covering of the treated trabecular meshwork with untreated conjunctiva.

In other implementations, after application, as shown in FIG. 4, of some or all of the tissue treatments, the tissue surrounding the trabecular meshwork can be rotated in the opposite direction to a greater extent than that to which it was first rotated, such as rotation in the counter-clockwise direction about 1 up to 90 degrees. Following any of the rotations or shifts of the tissue surrounding the trabecular meshwork described herein, and/or at any intermediate step, part or all of the tissue surrounding the trabecular meshwork being altered may be held using any known temporary or permanent means such as an applinator, pressure or other external force.

In further implementations, after application of some or all of the tissue treatments, the tissue surrounding the trabecular meshwork can be rotated in the opposite direction to a greater extent than that to which it was first rotated, such as rotation in the counter-clockwise direction about 1 up to 90 degrees. Following any of the rotations or shifts of the trabecular meshwork or surrounding tissues described herein, and/or at any intermediate step, part or all of the tissue surrounding the trabecular meshwork being altered may be held with any known temporary or permanent means as previously mentioned.

Another implementation may utilize multiple (e.g., 3) ablation zones (unlike the FIG. 1 one-treatment pass using a treatment energy size (e.g., spot size) with a diameter (and/or maximum dimension) ranging about 600-1000 microns (and/or using an output tip having a diameter of about 600-1000 microns)). Here, a threefold number of required treatments relative to the previous embodiment may correspond to an ablation zone about one third the size due to the size of the canula being about one third the size.

Multiple treatment passes may be utilized (e.g., beneficial) with treatment energy ranging from 200-600 microns. A treatment pass may be utilized (e.g., beneficial) due to the different requirements for ablation of the conjunctiva, sclera and trabecular meshwork. The ablation of different tissues requires (e.g., may be performed more optimally with) different treatment energies. The better matched the structure is to the ablation energy, the less collateral damage the adjacent structures should have, resulting in faster healing, less invasiveness and more efficacy.

Because of the nature of this all-laser procedure, the smaller the entry point the better healing the patient traditionally has. However, one cannot make the treatment point so small as to lose the ability to ablate the trabecular meshwork and have the appropriate amount of trabecular meshwork ablated in an optimal time window and fashion. Because the laser energy must pass through the conjunctiva and sclera in order to gain access to the trabecular meshwork, up to 3 levels of tunneling due to the different attributes of the structures overlying and adjacent to the trabecular meshwork such as the conjunctiva and sclera. One pass may be possible if the energy is able to precisely ablate the conjunctiva, sclera and trabecular meshwork without causing any damage to adjacent structures. Since the insertion point must go through the conjunctiva, it is imperative (e.g., optimal) that the thermal damage be kept to a minimum on this structure because (unlike the ablation to the trabecular meshwork which should not close), the conjunctiva should heal up and close.

Multiple ablations can be made, resulting in the kerf. For example, three ablations can form a kerf and may be different powers or sizes as deemed appropriate. This would allow a selective amount of trabecular meshwork to be left in place. Following an initial rotation of the tissue surrounding the trabecular meshwork multiple ablations may be made via application of one or more tissue treatments (e.g., a tissue treatment in the shape of a radially-extending spot or a row of tissue treatments forming the spot) made as one or more tissue treatments (e.g., elongate kerf(s) or apertures) in the trabecular meshwork, The tissue surrounding the trabecular meshwork can then be rotated in the same direction to a greater extent than that to which it was first rotated. One or more tissue treatments (e.g., a tissue treatment in the shape of a radially-extending spot or a row of tissue treatments forming the spot) can again be formed in the tissue surrounding the trabecular meshwork such as the conjunctiva or sclera through the same tissue treatments already formed in the tissue surrounding the trabecular meshwork so that the surrounding tissue is minimally impacted. FIG. 11 depicts an additional process that can be repeated to form additional tissue treatments of, for example, the same shape in the trabecular meshwork, through the same tissue treatments already formed in the tissue surrounding the trabecular meshwork. In this example, the tissue surrounding the trabecular meshwork is progressively rotated in one direction with tissue treatments being formed through the same opening(s) in the tissue surrounding the trabecular meshwork at each step. In modified embodiments, the tissue surrounding the trabecular meshwork can be rotated in the opposite direction (e.g., past the original, naturally-occurring orientation) to various degrees to facilitate formation of one or more tissue treatments (e.g., a tissue treatment in the shape of a radially-extending spot or a row of tissue treatments forming the spot) in the tissue surrounding the trabecular meshwork through the same tissue treatments already formed in the trabecular meshwork so that the surrounding tissues are minimally impacted again. Accordingly, the tissue over the trabecular meshwork can be rotated in both directions to facilitate formation of various tissue treatments in the tissue surrounding the trabecular meshwork, all through the same opening (e.g., tissue treatment) in the trabecular meshwork. As a result of the reduced number of tissue treatments being formed in the trabecular meshwork, redness and/or healing time can be attenuated or eliminated.

With continued reference to FIGS. 1-4, a camera or gonio lens or other visualization mechanism may not be required due to the ability of the aiming beam, e.g. green, to illuminate the treatment trajectory (for perception by the eye of a user) through or beneath the conjunctiva, sclera and trabecular meshwork. FIG. 3 shows insertion through the outer sclera flap in a direction that is perpendicular to the area of the trabecular meshwork that is to be treated allowing for a better field of vision with the aiming beam for orientation in determining the treatment area of the trabecular meshwork. Ablation of a portion of the trabecular meshwork can cause an area immediately tangent (and/or beneath) to be opened. FIG. 4 depicts the flow of aqueous humor even though the conjunctiva has been released (e.g. closed) over the insertion point, whereby the tissue treatments in the trabecular meshwork and surrounding tissues may be closed using techniques known in the art such as glue, sutures, surgical tacks, screws or staples, and/or applinator-style attachments including adhesives. In modified embodiments, one or more of the steps shown in FIGS. 2 and 3, and/or the closure step of FIG. 4, for example, may be attenuated, enhanced, or omitted, in whole or in part. A tissue glue such as tisseal may be used to close the laser incision on the sclera and conjunctiva, or closure may not be necessary due to the small nature of the incision and properties of the treatment energy In one example, rotation of the conjunctiva in a clockwise direction and multiple ablations results in ablation 1 zone being the conjunctiva, ablation zone 2 being the sclera, and ablation zone 3 being the trabecular meshwork. For example, a different laser paradigm (e.g., wavelength and/or power density suited for absorption of the corresponding zone such as a diode laser to ablate the conjunctiva and an Er:YSGG for the sclera and an Nd:YAG for the trabecular meshwork). The energy penetrates to the trabecular meshwork above the iris. An open area results from the ablation of the trabecular meshwork. Following ablation, the conjunctival tissue is rotated back and the closure of the conjunctiva is relatively separated from (e.g., not proximal to or in a relatively spaced proximity to) the treatment site due to the rotation. The tissue treatments in the trabecular meshwork and/or tissue surrounding the trabecular meshwork, according for instance to any of FIGS. 1-4, can comprise, for example, elongated and/or aperture-shaped tissue treatments such as those shown in the present examples of FIGS. 1-4, and/or may comprise groupings of tissue-treatments as discussed in any of the previously-mentioned examples, or combinations and permutations thereof, in various positions, shapes and patterns (e.g., fewer or greater numbers of elongated tissue treatments, of the same or different lengths). For instance, one or more (e.g., each) of the shown tissue-treatment elongated shapes may comprise, instead of an elongated kerf as shown. The kerf(s) illustrated in FIG. 7 show that the pattern may be dashed or solid and may range from a length of 1-20 mm, with exemplary widths of about 1 mm and exemplary depths of about 10 mm.

A series of smaller tissue treatments forming, for example, the same general shape is elucidated in FIG. 8. Moreover, one or more of the tissue treatments in the trabecular meshwork and/or surrounding tissue may comprise varying (e.g., reduced) sizes relative to the corresponding tissue treatments formed therebeneath in the tissue surrounding the trabecular meshwork, as elucidated in the illustrated examples of FIGS. 7-8. The treatment energy may be able to pass through tissues such as the conjunctiva and sclera and only ablate the trabecular meshwork via a tunneling effect such as described in the above-referenced U.S. Pat. No. 7,878,204 (Att. Docket BI9870P) and/or a defocusing/focusing effect (e.g., an excimer laser may be used to implement the treatment energy).

FIG. 7 shows the energy penetrating through the conjunctiva and sclera then onto the trabecular meshwork (e.g., in a line pattern). FIG. 7 shows the second pattern that has the insertion point over the trabecular meshwork through the conjunctiva. The pattern could be a solid line, dotted line or a kerf that extends to ablate the trabecular meshwork. FIG. 8 shows the ablation zone of the trabecular meshwork resulting in a kerf by entering the trabecular meshwork through the single point through the conjunctiva and sclera then proceeding one direction into the trabecular meshwork then rotating 180 degrees before proceeding once again into the trabecular meshwork. The incision made into the conjunctiva through the sclera will be used to begin the incision that proceeds along the trabecular meshwork in a clockwise direction.

With particular reference to FIG. 9, this sequence depicts a process locations for formation of tissue treatments are marked on the trabecular meshwork or surrounding tissue (1) and (2), and followed by the trabecular meshwork being moved (e.g., rotated or torqued) or shifted in some way or to some degree (3). The trabecular meshwork can, for example, be contacted with a template (2). Regarding the movement step, the trabecular meshwork can, for example, be contacted (e.g., gripped) using a trabecular meshwork location identifying template device (not shown) and moved.

In FIG. 9 tissue treatments can be formed in the trabecular meshwork and/or tissue surrounding the trabecular meshwork at locations corresponding to the post-movement positions of the markings, and the trabecular meshwork can once again be moved (e.g., rotated, torqued and/or shifted) in some way or to some degree. For example, the tissue surrounding the trabecular meshwork can be moved (e.g., rotated, torqued and/or shifted) in some way or to some degree so that the tissue treatments formed in the tissue surrounding the trabecular meshwork are at least partially, and in certain embodiments, completely, covered by non-tissue-treatment areas of the trabecular meshwork and/or tissue surrounding the trabecular meshwork.

Pressure may be applied to the conjunctiva, and because of the elasticity it will move to expose the treatment area (e.g., typically the sclera and trabecular meshwork). Rotating the conjunctiva either clockwise or counter-clockwise allows the treatment area underneath such as the sclera and trabecular meshwork to be covered by a non-treated conjunctiva therefore providing more nutrients to the treated area which will aid in both patient comfort and healing. According to certain embodiments, the untreated conjunctiva can be moved back over the treatment site to cover the treated area of the trabecular meshwork. (to the same, lesser or greater extent) in a direction from which it was first moved, but in modified embodiments it may be moved at least in part (to the same, lesser or greater extent) in other directions. As presently embodied, the tissue surrounding the trabecular meshwork can be rotated so that the angular locations of the markings are changed from their post-movement angular positions, and in the illustrated example of FIG. 9 the tissue surrounding the trabecular meshwork is rotated so that angular locations of the markings are changed back to locations corresponding to the pre-movement positions of the markings corresponding for example to the naturally-occurring orientation of the trabecular meshwork. The tissue surrounding the trabecular meshwork can be moved using for example the trabecular meshwork identifying template device. Following any of the movements of the tissue surrounding the trabecular meshwork described herein, and/or at any intermediate step, part or all of the trabecular meshwork being altered may be held with any herein-described or known temporary or permanent means, such as the trabecular meshwork identifying template device.

In certain embodiments, fluids, including water, sterile water or conditioned fluids may be added to ensure or aid in the cosmetic appeal of the treated tissue and/or to assist with healing time or other properties. For example, fluid (e.g., sterile water) may be applied by way of a small air mister (e.g., from a local or remotely-disposed canister or dropper) affixed, for example, to a device (e.g., an applinator device or output tip), between or, preferably, during application of treatment energies, to thereby attenuate or eliminate charring and/or wash away blood. As another example, fluid (e.g., sterile water) may be applied by way of a small air mister or sprayer spot affixed, for example, to a treatment energy (e.g., laser) device (e.g., handpiece) at or for any of the above-noted times or purposes. The spot may comprise, for example, tubing (e.g., clip-on and/or silicone based tubing) secured to an outside or built into the device and a fluid dispensing input disposed on the device. The fluid-dispensing input may be activated, for example, to facilitate manual or powered dispensation of fluid. Manual dispensation may be implemented by way of, for example, a spot leading to or integrally formed with a detachable container (e.g., pod) that can be squeezed by a user to dispense fluid (e.g., sterile water pre-packaged into a single-use, disposable pod), and powered dispensation may be implemented by way of a toggle button to initiate a powered output of fluid at, for example, a relatively low flow rate and pressure. An atomized distribution of fluid (e.g., sterile water) particles may be automatically applied to the target tissue during application of treatment energies, for example. In other examples, a drop of the fluid (e.g., sterile water) may be applied before or during application of treatment energies. In still further embodiments, treatment energies and fluid (e.g., sterile water) may be combined to facilitate electromagnetically induced mechanical cutting, as described in the preceding two patents, to enhance cutting attributes. Suction may be applied to any of the foregoing implementations, as well, for removing fluids, debris and/or liquids. For any embodiments employing suction for any purpose described herein, such as to secure a structure to a surface of the eye, specialized surfaces (e.g., relatively non-porous surfaces to facilitate suctional gripping and securement of the structure to the eye) and/or surface treatments (e.g., the above-mentioned Viscasil®) can be employed.

Referring to FIGS. 10a-10d, a process is shown wherein tissue treatment markings are formed in surrounding tissue over the trabecular meshwork at exemplary locations. As depicted in FIGS. 10a-10d, locations for generation of tissue treatments can be disposed on the trabecular meshwork in sets (e.g., pairs). One or more (e.g., all) of the sets can comprise, for example, a plurality of tissue treatments or tissue treatment groupings as described above, wherein the tissue treatments or tissue treatment groupings of one or more of the sets are configured to allow interweaving with one or more of the subsequently formed tissue treatments or tissue treatment groupings in the tissue surrounding the trabecular meshwork. In the illustrated embodiment, the tissue treatments or tissue treatment groupings of the sets allow interweaving with the subsequently formed tissue treatments or tissue treatment groupings in the tissue surrounding the trabecular meshwork. As presently shown, the tissue treatments or tissue treatment groupings of each set are spaced one from the other at different (e.g., greater) distances than for example those shown in FIGS. 10a-10d. For instance the treatment pattern may comprise spots close together or far apart (e.g., spaced 0.1 mm to 1 mm apart) and may vary in spot sizes (e.g., in diameter from 0.1 mm to 1 mm) as long as it will work to ablate the trabecular meshwork. In a particular instance, FIGS. 10a-10d may be considered relative to one another as being to scale.

In FIGS. 10a-10d the tissue surrounding the trabecular meshwork is moved (e.g., rotated or torqued) or shifted in some way or to some degree as described above. The tissue surrounding the trabecular meshwork can for example be contacted (e.g., gripped) using a trabecular meshwork identifying template device and moved as described above. The tissue surrounding the trabecular meshwork can be rotated so that angular locations of the markings are changed from their pre-movement marked angular positions and, as presently illustrated, so that the post-movement angular location(s) of at least one of the markings of each set is disposed between two of the pre-movement locations of the markings of a corresponding set. According to the implementation illustrated in FIG. 10b, the post-movement angular location one of the markings of each set is disposed between two of the pre-movement marking locations of the corresponding set. For instance the treatment pattern may be close together or far apart 0.1 mm to 1 mm and may vary in spot sizes from 0.1 mm to 1 mm but will work to ablate the trabecular meshwork. In FIG. 10c the tissue treatments can be formed in both the trabecular meshwork and tissue surrounding the trabecular meshwork at locations corresponding to the post-movement positions of the markings as described above, and in FIG. 10d the tissue surrounding the trabecular meshwork can be moved as described above and the tissue treatments in the trabecular meshwork closed as discussed above. Modified embodiments similar to those discussed above in connection with FIGS. 1-4 may be implemented, as well.

FIG. 11 depicts a particular implementation of treatment patterns wherein tissue-treatment markings are formed on the tissue surrounding the trabecular meshwork for treatment-energy delivered in a variety of patterns or formations. Rotating and/or torquing may be omitted in FIG. 11. In FIG. 11 the tissue surrounding the trabecular meshwork is rotated or torqued in a counter-clockwise direction twenty to thirty degrees back to its naturally-occurring orientation, followed by the tissue treatments in the tissue surrounding the trabecular meshwork being closed as discussed above.

Regarding the aperture-shaped tissue treatment markings (and/or tissue treatments) on (in) the trabecular meshwork, the sizes and shapes of these items can be formed, for example, to be as small as possible while still enabling, for example, formation of corresponding tissue treatments or tissue treatment groupings there beneath in the tissue of and/or surrounding the trabecular meshwork. In the illustrated embodiment, the tissue treatment markings on and tissue treatments in the tissue of and/or surrounding the trabecular meshwork comprise circular shapes approximating the cross-section of (e.g., and formed by) a fiber optic tip that can, in the illustrated embodiment, be used to form the tissue treatments in the underlying tissue of and/or surrounding the trabecular meshwork (e.g. an excimer laser may be used to implement the treatment energy)

Formation of tissue treatments in the trabecular meshwork and tissue surrounding the trabecular meshwork using a laser as depicted in FIGS. 6A-B be accomplished using various apparatuses and techniques, exemplary approaches including one or more of: (a) separating the conjunctiva from the tissue surrounding the sclera by injecting a fluid such as an epinephrine-based fluid therebetween via a needle entry point in a vicinity of the limbus prior to treatment with a spot size of approximately 200 microns; (b) inserting a fiber optic tip through a tissue treatment located through the conjunctiva and sclera with a spot size of approximately 300 microns then maneuvering the treatment energy approximately midway along a length of an underlying trabecular meshwork with a treatment (e.g., elongated kerf) or tissue treatment grouping (e.g., collection of relatively small tissue treatments approximating, or bounded by, shapes of the illustrated elongated kerfs) and then forming the tissue treatment or tissue treatment grouping in the tissue surrounding the trabecular meshwork by, for example, changing an orientation of the fiber optic tip as shown in the cross-sectional view of FIGS. 10A-10B; and (c) inserting a fiber optic tip through a tissue treatment located in a vicinity anywhere tangent to the trabecular meshwork (and/or including) the conjunctiva and sclera midway at a point midway along a length of an underlying trabecular meshwork via treatment or tissue treatment grouping with a cutting/slicing spot size of approximately 400 microns.

An exemplary implementation of the (a) approach can comprise a surgeon selecting a minimum amount of anesthesia needed to keep the patient comfortable, with the anesthesia comprising at least one of the following local anesthetics: 1% Tetracaine applied in a circular ring pledget around the ciliary body for five minutes; local subtenon's injection with 2% Lidocaine applied one quadrant at a time; and topical 2% Xylocalne gel applied 20-30 minutes prior to surgery. Topical 1% Proparacaine can be applied 5 minutes before the procedure and periodically during the procedure as deemed appropriate by the surgeon according to the patient's pain response. Topical 1% Tetracaine or 2% Lidocaine can also be used. A peribulbar injection comprising a 50/50 mixture of 2% Lidocaine with 0.75% Marcaine can be administered according to the clinical judgment of the investigator if the patient does not obtain effective anesthesia by any of the above methods. One drop of a topical antibiotic (Vigamox, Ciloxan or Zymar) and one drop of a topical non-steroidal anti-inflammatory (Acular LS or Voltaren) can also be applied. The patient can be prepared according to typical protocols for refractive surgery, with a lid speculum being inserted followed by placement of a cornea protector over the cornea.

In connection with any of the rotations and/or shifts of the trabecular meshwork described herein, and/or at any pre-operative or intermediate step, part or all of the trabecular meshwork being altered may be treated to, for example, to control heat.

In another example, cooled matter (e.g., fluid) may be applied to reduce heat by way of an encouragement of constriction of blood vessels. The cooled matter (e.g., air and/or water below room temperature) may be applied to a tissue, for example, to control heat, which heat may have been caused by cutting, ablating, or other trauma inflicted on the tissue. Such cooled matter (e.g., fluid, gel, ice pack) may be applied, for example, to an eye to slow or stop heat following an ablation procedure, such as a cutting procedure performed with a laser. As examples, cooled matter may be applied before, during, or after any of the steps described herein that may cause heat.

For instance, cooled matter may be applied to the eye in connection with procedures involving rotating or shifting the ocular tissue.

Care may be taken when rotating or shifting the ocular tissue to attenuate tissue damage, such as de-vascularization and/or necrosis, resulting from, for example, excessive movement of the trabecular meshwork. In certain embodiments, portions of the trabecular meshwork to be moved may be separated from underlying tissue using known techniques, to thereby facilitate greater movement of the trabecular meshwork while controlling tissue damage. According to certain implementations, a fluid, such as an epinephrine-based fluid (e.g., anesthetic and/or vasal constrictor) may be introduced (e.g., in a vicinity of a boundary of the trabecular meshwork and one or more of the cornea, the choroid, and the ciliary muscle) before substantial movement and/or before separation from underlying layers of the trabecular meshwork. In modified embodiments, the fluid may have a viscosity greater than water. For instance, the fluid may comprise a gel, such as a transparent, water based gel.

Following any of the rotations and/or shifts of the trabecular meshwork described herein, and/or at any intermediate step, part or all of the trabecular meshwork being altered may be held with any known temporary or permanent means. For example, following movement back to, or back to and then slightly beyond, its naturally-occurring orientation, sutures, surgical tacks, screws or staples, and/or applinator-style attachments including adhesives may be applied to hold the trabecular meshwork in place.

Torquing or rotating of the trabecular meshwork may be possible using any of a variety of methods and devices. While aqueous humor is formed almost entirely of liquid, the conjunctiva is vascular and thus should be handled carefully, for example, to minimize heat. Heat can cause a change in the tissue. In order to keep the tissue viable it is necessary to protect the tissue structures by minimizing heat. The conjunctiva may also be capable of being extensively stretched. Regarding movement of the conjunctiva gland, as presently illustrated, the trabecular meshwork can be rotated using, for example, a tool, so that the angular locations of the markings are changed from their initial (i.e., pre-movement) marked angular positions. Following such movement (e.g., rotation), the trabecular meshwork may be held in the post-movement position using, for example, a trabecular meshwork template device while some or all of the tissue treatments are subsequently applied.

Before torquing the trabecular meshwork surrounding tissue, the trabecular meshwork may be, for example, ballooned with a fluid. For instance, a fluid (e.g., comprising epinephrine) may be inserted beneath the trabecular meshwork, to thereby separate the trabecular meshwork from the underlying tissue surrounding the trabecular meshwork.

A pair of incisions (e.g., top and bottom incisions) may be formed in the trabecular meshwork, and a tool having a pair of opposing legs may be inserted between the trabecular meshwork and the tissue surrounding the trabecular meshwork.

Suction may be applied to the contacting portion, wherein the contacting portion may be constructed and operated as described in connection with FIGS. 6A-6B In one illustrative example, movement of the output tip from the center area of the transverse slot in the first direction moves the trabecular meshwork (e.g., a portion of the trabecular meshwork) in the first direction and movement of the output tip from the center area of the transverse slot in the second direction move the trabecular meshwork (e.g., a portion of the trabecular meshwork) in the second direction. According to another illustrative example, movement of the output tip from the center area of the transverse slot in the first direction moves a portion of the trabecular meshwork a corresponding (e.g., approximately equal) distance in the first direction, and movement of the output tip from the center area of the transverse slot in the second direction moves a portion of the trabecular meshwork a corresponding (e.g., approximately equal) distance in the second direction. Thus, the trabecular meshwork can be moved (e.g., rotated or torqued) or shifted in two opposing directions to facilitate formation of two different tissue treatments in the underlying tissue surrounding the trabecular meshwork.

According to modified embodiments, groupings of tissue treatments may be disposed around cuts (e.g., kerfs) to the tissue surrounding the trabecular meshwork implemented in accordance with other technologies. In other modified embodiments, as an alternative or addition to any of the embodiments described herein, tissue treatments may be arranged to approximate or resemble prior-art surgical-formation shapes. In implementations wherein tissue treatments are applied in combination with one or more of the patterns or ablation patterns disclosed in the aforementioned patent, the tissue treatments can be disposed for example along part or all of the boundary(ies) of the linear ablation pattern(s) with or without the ablation pattern(s) being formed as well. In modified embodiments, any of the above tissue treatments may be applied in combination with any other eye treatments to the extent compatible, or modifiable to be compatible, by one skilled in the art, with the present tissue treatments. For instance, the presently-described alterations (e.g., rotations and/or shifts) to the tissue surrounding the trabecular meshwork in connection with the formation of tissue treatments in the trabecular meshwork or surrounding tissue may be modified and/or combined with other technologies (e.g., such as described in the aforementioned patent) involving applications or formations of treatments (e.g., ablations) to the trabecular meshwork.

What is claimed is:

1. A method of reducing intraocular pressure in an eye, comprising:
    making a perpendicular incision through a conjunctiva of the eye to access a trabecular meshwork of the eye;
    focusing electromagnetic energy through the perpendicular incision to ablate a portion of the trabecular network meshwork, wherein said ablation creates to create a channel for outflow flow of fluid through a sclera venous sinus to reduce pressure within the eye; and
    projecting a visible light pattern onto a portion of the eye, wherein the electromagnetic energy is focused through the visible light pattern to make the perpendicular incision or to ablate the portion of the trabecular meshwork using the visible light pattern as a guide;
    wherein the focusing includes
        performing a first ablation to make the perpendicular incision through the conjunctiva,
        performing a second ablation to make an incision in a sclera of the eye, and
        performing a third ablation to ablate the portion of the trabecular meshwork.

2. The method of claim 1, wherein the electromagnetic energy is focused using a laser tip, wherein the laser tip is inserted through the perpendicular incision, and wherein the laser tip is transited around the lens without crossing the lens while focusing the electromagnetic energy to ablate portions of the trabecular network meshwork.

3. The method of claim 1, wherein the electromagnetic energy is focused using a laser tip, wherein the laser tip is inserted through the perpendicular incisions, and wherein the laser tip is not moved transverse across the width of a lens of the eye.

4. The method of claim 1, wherein the conjunctiva begins at a rested position, wherein the method further includes: rotating the conjunctiva from the rested position to a rotated position prior to making the perpendicular incision; and releasing the conjunctiva from the rotated position to the rested position following ablation of the portion of the trabecular network meshwork.

5. The method of claim 4, wherein, when the conjunctiva is in the rested position, the perpendicular incision is further from the ablated portion of the trabecular network meshwork than when the conjunctiva is in the rotated position.

6. The method of claim 1, wherein the electromagnetic energy is generated using a laser.

7. The method of claim 1, wherein said the electromagnetic energy is focused in a pattern to ablate a plurality of holes in the trabecular network meshwork.

8. The method of claim 7, wherein the pattern is formed using a computer-implemented scanner.

9. The method of claim 7, wherein the electromagnetic energy is focused using a laser tip, and wherein the electromagnetic energy is focused such that the plurality of holes are ablated simultaneously.

10. The method of claim 1, wherein the perpendicular incision is further made through a sclera of the eye.

11. The method of claim 1, wherein the perpendicular incision is made substantially perpendicular to the surface of the eye.

12. The method of claim 1, wherein the energy is focused to ablate portions of the trabecular network meshwork in a form of a line.

13. The method of 1, wherein the fluid is aqueous humor, wherein excess aqueous humor in the eye results in increased intraocular pressure that increases the risk of glaucoma in the eye.

14. A method, comprising:
  (i) making a perpendicular incision through a conjunctiva of the eye to access a trabecular meshwork of the eye;
  (ii) applying treatment energy to the trabecular meshwork along a first circumferential ablation path extending around a lens of the eye from a start location adjacent the lens to a first end location adjacent the lens; and
  (iii) applying the treatment energy to the trabecular meshwork along a second circumferential ablation path extending around the lens from the start location, away from the first circumferential ablation path, to a second end location adjacent the lens; wherein the method reduces intraocular pressure in the eye.

15. The method of claim 14 wherein step (ii) includes applying the treatment energy from the start location toward the first end location along the first circumferential ablation path, and step (iii) includes applying the treatment energy from the start location toward the second end location along the second circumferential ablation path.

16. The method of claim 14 wherein, in steps (i) and (ii), the treatment energy is emitted from a laser tip, and wherein step (i) includes moving the laser tip from the starting location in the first direction along the first circumferential path; and wherein step (ii) includes moving the laser tip from the starting location in the second direction along the second circumferential path.

17. The method of claim 16 further comprising, between steps (i) and (iii): retracting the laser tip along the first circumferential path back to the start position.

18. The method of claim 16 further including, after step (iii): retracting the laser tip along the second circumferential path back to the start position.

19. The method of claim 16 wherein the laser tip is configured to bend while in the eye.

20. The method of claim 16 wherein the ablation paths in steps (ii) and (iii) are each 90 degrees.

21. The method of claim 16 wherein a sum of the ablation paths of steps (ii) and (iii) exceeds 180 degrees.

22. The method of claim 14 wherein the electromagnetic energy is generated by a laser.

\* \* \* \* \*